(12) United States Patent
Baker et al.

(10) Patent No.: US 10,842,884 B2
(45) Date of Patent: Nov. 24, 2020

(54) ENDOSOMOLYTIC AGENTS FOR GENE THERAPY

(71) Applicant: UCB Biopharma SRL, Brussels (BE)

(72) Inventors: Terence Seward Baker, Slough (GB); Michael Anthony William Eaton, Watlington (GB); Timothy John Norman, Slough (GB); James Petrie Turner, Slough (GB)

(73) Assignee: UCB Biopharma SRL, Brussels (BE)

( * ) Notice: Subject to any disclaimer, the term of this patent is extended or adjusted under 35 U.S.C. 154(b) by 0 days.

(21) Appl. No.: 16/337,243

(22) PCT Filed: Sep. 27, 2017

(86) PCT No.: PCT/EP2017/074543
§ 371 (c)(1),
(2) Date: Mar. 27, 2019

(87) PCT Pub. No.: WO2018/060280
PCT Pub. Date: Apr. 5, 2018

(65) Prior Publication Data
US 2019/0298859 A1    Oct. 3, 2019

(30) Foreign Application Priority Data

Sep. 29, 2016  (GB) .................................. 1616563.1

(51) Int. Cl.
| | | |
|---|---|---|
| *C07F 9/117* | (2006.01) | |
| *C07F 9/12* | (2006.01) | |
| *C07J 51/00* | (2006.01) | |
| *A61K 48/00* | (2006.01) | |
| *C07F 9/10* | (2006.01) | |

(52) U.S. Cl.
CPC ...... *A61K 48/0008* (2013.01); *A61K 48/0066* (2013.01); *A61K 48/0083* (2013.01); *A61K 48/0091* (2013.01); *C07F 9/106* (2013.01); *C07F 9/117* (2013.01); *C07F 9/12* (2013.01); *C07J 51/00* (2013.01)

(58) Field of Classification Search
CPC ............ A61K 48/0008; A61K 48/0091; A61K 48/0066; A61K 48/0083; C07F 9/117; C07F 9/106; C07F 9/12; C07J 51/00
USPC ............ 514/182, 144, 148; 552/506; 554/79
See application file for complete search history.

(56) References Cited

U.S. PATENT DOCUMENTS

2008/0306153 A1    12/2008 Panzner et al.

FOREIGN PATENT DOCUMENTS

| EP | 0316117 | 5/1989 | |
|---|---|---|---|
| WO | WO-2004067483 A2 * | 8/2004 | ................ C07F 9/10 |

OTHER PUBLICATIONS

Thomas et al., "Tuning the response of a pH-sensitive membrane switch", Journal of the American Chemical Society, vol. 117, No. 10, Mar. 1, 1995, pp. 2949-2950.
Database Chemcats, Chemical Abstracts; Sep. 21, 2017, Database accession No. 1295056312.
Database Chemcats, Chemical Abstracts; Mar. 29, 2017, Database accession No. 1229531411.
Database Chemcats, Chemical Abstracts; Mar. 29, 2017, Database accession No. 0734056117.
Database Chemcats, Chemical Abstracts; Mar. 27, 2017, Database accession No. 0645480429.
Golebiewski et al., Bioorganic & Medicinal Chemistry (1996); 1637-1648.
Karmali et al., Med. Res. Rev., (2007); 27:696-722.
Li et al., Gene Ther., (2006); 13:1313-1319.
Friend et al., Biochimica et Biophysica Acta, (1996); 1278:41-50.
Devine et al., Advanced Drug Delivery Reviews (1998); 32:19-29.
Ogris et al., Gene Ther., (1999); 6:595-605.
Semple et al., Advanced Drug Delivery Reviews, (1998); 32:3-17.
Mori et al., Journal of Liposome Research, (1998); 8:195-211.
Wu et al., Biochimica et Biophysica Acta, (1996); 1284:13-19.
Smith et al., Advanced Drug Delivery Reviews, (1998); 30:115-131.
Saccardo et al., Biotechnol. Adv., (2009); 27:432-438.
Godbey et al., Journal of Biomedical Materials Research, (2000); 51:321-328.
Shangguan et al., Gene Ther., (2000); 7:769-783.
Saminathan et al., Nucleic Acids Research, (2002); 30:3722-3731.
Sorgi et al., Gene Ther., (1997); 4:961-968.
Legendre et al., Bioconjugate Chem., (1997); *, 57-63.
Israelachvili, Q. Rev. Biophys., (1980); 13:121.
Evans, Langmuir, (1988); 4:3.
Regen, J. Am. Chem. Soc., (1993); 115:2278.

(Continued)

*Primary Examiner* — Matthew P Coughlin
*Assistant Examiner* — Sagar Patel
(74) *Attorney, Agent, or Firm* — McDonnell Boehnen Hulbert & Berghoff LLP

(57) ABSTRACT

Compounds of formula (I), wherein Ar is an aryl group optionally further substituted with one or more groups $R^3$; A is a lipophilic, hydrophobic moiety; $R^1$ is a phosphodiester, phosphotriester, thioether or amide group; X is an unsubstituted or substituted $C_6$ to $C_{24}$ alkylene or alkenylene group, which is optionally interrupted by one or more —$NR^9$—, —O— or —S— linkages, $R^2$ is —$YC(R^4)(R^5)CO_2R^6$; and pharmaceutically acceptable salts or solvates thereof are useful as endosomolytic agents particularly for the delivery of nucleic acids useful in gene therapy.

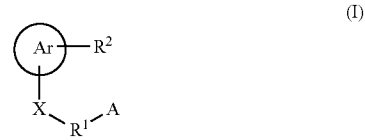

(I)

21 Claims, 2 Drawing Sheets

(56) References Cited

OTHER PUBLICATIONS

Evans, Biochem J., (1985): 232:33.
Regen, J. Am. Chem. Soc., (1990); 112:5851.
International Search Report for International Application No. PCT/EP2017/074543 dated Feb. 7, 2018, 3 pages.

* cited by examiner

ENDOSOMOLYTIC AGENTS FOR GENE THERAPY

This application is a U.S. national phase application under 35 U.S.C. § 371 of International Patent Application No. PCT/EP2017/074543, filed Sep. 27, 2017, which claims the benefit of priority of Great Britain Patent Application No. 1616563.1, filed Sep. 29, 2016.

The present invention relates to compounds useful as endosomolytic agents in gene therapy, to pharmaceutical compositions comprising them and to their use in medicine.

BACKGROUND TO THE INVENTION

Nucleic acids have huge potential as therapeutic agents. However, the facile delivery of nucleic acids to the cell nucleus is a barrier to their widespread use in medicine. Polar macromolecules such as nucleic acids are unable to simply cross the lipophilic cell membrane, unlike small lipophilic molecules for which this is a simple process. In nature, polar molecules are transported by active transport, endocytosis and phagocytosis. It is believed that macromolecules such as nucleic acids and proteins are transported by endocytosis and end up inside membrane bound compartments within the cell, known as endosomes. As a result of the proton pump, these endosomes become acidified, before the contents are hydrolysed, resulting in the degradation of the nucleic acid within.

Small molecules which perturb the endosomal membrane without provoking an immune response may be utilised to aid the delivery of a nucleic acid vector to the nucleus. In addition, suitable molecules must selectively perturb the membrane of the acidic endosome, as opposed to any membrane which they come into contact with inside the body.

Reagents which disrupt lipid bilayers typically do so due to surfactive properties. The presence of a polar, hydrophilic domain and a non-polar, lipophilic domain results in them locating at the interface between the lipid bilayer and the aqueous environment. The molecules which form the present invention comprise a tertiary carboxylic acid which is highly polar when ionised, but sufficiently non-polar when protonated to be partitioned into the organic phase of an aqueous/organic biphasic system. Hence, these molecules will change conformation in the lower pH of an endosome, resulting in them having endosomolytic properties, and hence allowing a polar macromolecule to cross the membrane into the cytoplasm. The efficacy of tertiary carboxylic acids for this purpose has been demonstrated in the art, see Thomas et al., J. Am. Chem. Soc., (1995) 117, pp. 2949-2950.

SUMMARY OF THE INVENTION

The present invention is directed to a new class of compounds which are believed to provide the ability to selectively perturb the lipid bilayer membrane of an endosome, allowing its contents to cross the membrane into the cytoplasm, thereby giving access to the nucleus. This perturbation is achieved by the compounds adopting a tapered shape and becoming lipophilic when in an environment of pH ~5 or below. The compounds with tapered shape can then interact with the uniform shaped constituent lipid of the bilayer, disrupting the structure and destabilising the membrane. At neutral pH the molecules are polar and do not adopt a tapered shape, and therefore do not interact with the membrane in such a way as to destabilise it. Hence, it is only at lower pH, such as that found inside an endosome that the compounds are able to disrupt the lipid bilayer of the membrane, and herein lies the selectivity of the compounds. Thus the compounds of the invention are believed to be useful in the delivery of nucleic acids to the nucleus by transfection. They may therefore be used in gene therapy.

The present invention therefore provides a compound of formula (I) or a pharmaceutically acceptable salt or solvate thereof

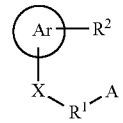

(I)

wherein
Ar is an aryl group optionally substituted with one or more groups $R^3$;
A is a lipophilic, hydrophobic moiety;
$R^1$ is a phosphodiester, phosphotriester, thioether or amide group;
X is an unsubstituted or substituted $C_6$ to $C_{24}$ alkylene or alkenylene group, which is optionally interrupted by one or more —$NR^9$—, —O— or —S— linkages, wherein $R^9$ is a $C_1$ to $C_6$ alkyl group;
$R^2$ is —$YC(R^4)(R^5)CO_2R^6$;
Y is a covalent bond or —$(CH_2)_m$— wherein m is 1, 2 or 3;
$R^4$ and $R^5$ are the same or different and each is a substituted or unsubstituted $C_1$ to $C_6$ alkyl, $C_2$ to $C_6$ alkenyl or $C_2$ to $C_6$ alkynyl group;
$R^6$ is a hydrogen atom or an unsubstituted or substituted $C_1$ to $C_6$ alkyl group; each $R^3$ moiety is the same or different and each is selected from a halogen atom, a $C_1$ to $C_6$ alkyl group, a $C_1$ to $C_6$ alkenyl group, a $C_1$ to $C_6$ alkynl group, a $C_1$ to $C_6$ alkoxy group, and —$YC(R^4)(R^5)CO_2R^6$, and wherein an $R^3$ moiety is —$YC(R^4)(R^5)CO_2R^6$ it may be the same or different to $R^2$;
wherein $R^4$, $R^5$ and $R^6$ are unsubstituted or substituted with one or more substituents selected from a halogen atom, a hydroxyl group, $C_1$ to $C_6$ alkoxy and —$NR^7R^8$ wherein $R^7$ and $R^8$ are the same or different and each is a $C_1$ to $C_6$ alkyl groups.

The present invention also provides a gene therapy vector comprising a compound in accordance with the invention as described above.

The present invention also provides a pharmaceutical composition comprising a compound in accordance with the invention as described above, or a pharmaceutically acceptable salt or solvate thereof, or a gene therapy vector comprising a compound of the invention as described above, and a pharmaceutically acceptable carrier or diluent.

The present invention also provides a compound in accordance with the invention as described above, a gene therapy vector comprising a compound of the invention, or a pharmaceutical composition of the invention for use in treating the human or animal body, for example in gene therapy.

The present invention also provides a compound in accordance with the invention as described above, a gene therapy vector comprising a compound of the invention, or a pharmaceutical composition of the invention for use in the treatment and/or prevention of a disorder by the administration of a gene therapy vector.

The present invention also provides use of a compound in accordance with the invention as described above or a gene therapy vector comprising a compound of the invention, in the manufacture of a medicament for use in gene therapy.

The present invention also provides a product containing a compound in accordance with the invention as described above and a gene therapy vector for simultaneous, separate or sequential use in gene therapy.

The present invention also provides a method for the treatment and/or prevention of a disorder for which the administration of a gene therapy vector is indicated which comprises administering to a patient in need of such treatment an effective amount of a compound in accordance with the invention as described above or an or a pharmaceutically acceptable salt or solvate thereof, in conjunction with a gene therapy vector.

In a particular embodiment the compounds of the invention may be useful in conjunction with a gene therapy vector for the prevention and/or treatment of oncological disorders.

DETAILED DESCRIPTION OF EMBODIMENTS OF THE INVENTION

Figure 1:
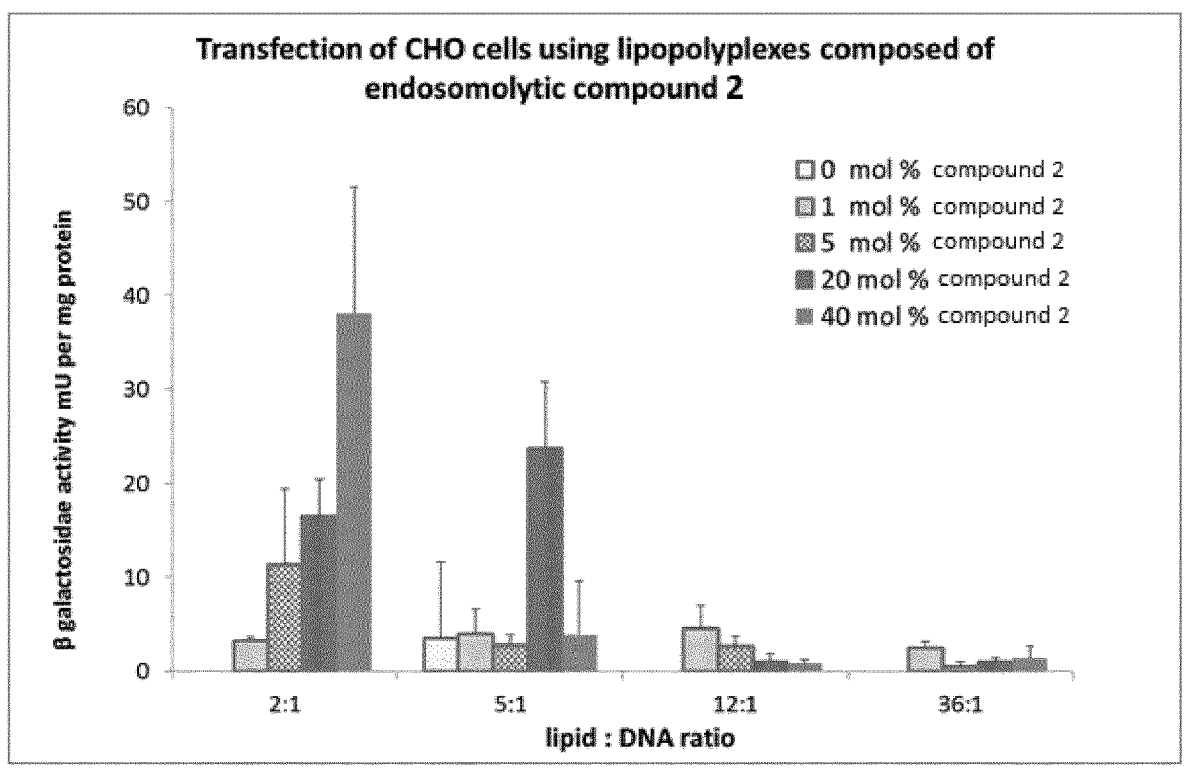
FIG. 1 shows the effect on reporter gene expression of varying the amount of an endosomolytic compound in a lipopolyplex, at different lipid:DNA ratios.

Where any of the groups in the compounds of formula (I) above is stated to be unsubstituted or substituted (or optionally substituted), this group may be unsubstituted, or substituted by one or more substituents. Typically, such groups will be unsubstituted, or substituted by one or two substituents.

The salts of the compounds of formula (I) which are useful in medicine will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of use in this invention include addition salts which may, for example, be formed by mixing a solution of the compound of use in the invention with a solution of a pharmaceutically acceptable base. Suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts. Furthermore, where the compounds of use in the invention carry a basic moiety, e.g. an amine group, suitable pharmaceutically acceptable salts thereof may include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of use in the invention include straight-chained and branched $C_{1-6}$ alkyl groups, for example $C_{1-3}$ alkyl groups, and straight-chained and branched $C_{10-20}$ alkyl groups. Typical examples of $C_{1-6}$ alkyl groups include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", are to be construed accordingly. Typical examples of $C_{10-20}$ alkyl groups are undecyl, hexadecyl and octadecyl.

Suitable alkenyl groups which may be present on the compounds of use in the invention include straight-chained and branched $C_{2-6}$ and $C_{10-24}$ alkenyl groups. Suitable alkenyl groups also include terminal alkenyl groups such as allyl and non-terminal alkenyl groups such as crotyl. Alkenyl groups may be cis- or trans-. Typical examples of $C_{2-6}$ alkenyl groups include vinyl and allyl groups, and straight-chained or branched, terminal or non-terminal, cis- or trans-butenyl, pentenyl and hexenyl groups. Particular alkenyl groups include vinyl and allyl.

Typical examples of $C_{10-24}$ alkenyl groups include straight chained, terminal or non-terminal, cis- or trans-alkenyl groups. More typically, they may comprise only trans- or terminal double bonds. Alkenyl groups may have as many double bonds as their length permits, typically one, two or three double bonds, more typically one double bond.

Suitable alkynyl groups which may be present on the compounds of use in the invention include straight-chained and branched $C_{2-6}$ alkynyl groups. Suitable alkynyl groups also include terminal alkynyl groups such as ethynyl and propargyl and non-terminal alkynyl groups such as but-2-ynyl. Typical examples include ethynyl and propargyl groups.

The term "alkylene" as used herein refers to bivalent saturated aliphatic groups derived from alkyl groups. Typically such groups are $C_{6-24}$ alkylene groups. Suitable alkylene groups include undecylene, dodecylene, tridecylene, tetradecylene, pentadecylene, hexadecylene, heptadecylene, octadecylene, nonadecylene and icosylene. Where the compounds in accordance with the invention comprise an optionally substituted straight or branched alkylene chain, such chains may be optionally substituted by one or more substituents. Suitably, such chains are unsubstituted, monosubstituted or disubstituted. Typically, such chains are unsubstituted or monosubstituted. In one embodiment, such chains are unsubstituted. In another embodiment, such chains are monosubstituted. In a further embodiment, such chains are disubstituted.

The term "alkenylene" as used herein refers to bivalent unsaturated aliphatic groups derived from alkenyl groups. Such groups may comprise cis- or trans-double bonds, and may comprise multiple double bonds. Typically such groups will comprise one, two or three double bonds, more typically one double bond. Such groups may be straight chained or branched. Typically such groups will be straight chained. Where the compounds in accordance with the invention comprise an optionally substituted straight or branched alkenylene chain, such chains may be optionally substituted by one or more substituents. Suitably, such chains are unsubstituted, monosubstituted or disubstituted. Typically, such chains are unsubstituted or monosubstituted. In one embodiment, such chains are unsubstituted. In another embodiment, such chains are monosubstituted. In a further embodiment, such chains are disubstituted.

The term "aryl" as used herein refers to $C_6$ to $C_{14}$ monovalent carbocyclic aromatic groups derived from a single aromatic ring or multiple condensed aromatic rings. Suitable aryl groups include phenyl, naphthyl and anthracyl, typically phenyl or naphthyl, more typically phenyl.

The term "halogen" as used herein is includes fluorine, chlorine, bromine and iodine atoms, typically fluorine, chlorine or bromine.

The term "phosphodiester" as used herein refers to a group of the formula O=P(OR)(OR')OH, wherein R and R' are carbon containing groups bonded to oxygen through a carbon atom, typically R and R' are selected from unsubstituted or substituted alkyl, alkenyl, alkynyl, alkylene, alkenylene and aryl groups. In particular R and R' are X and A as defined herein.

The term "phosphotriester" as used herein refers to a group of the formula O=P(OR)(OR')OR", wherein R, R' and R" are carbon containing groups bonded to oxygen through a carbon atom, typically R, R' and R" are selected from unsubstituted or substituted alkyl, alkenyl, alkynl, alkylene, alkenylene and aryl groups. In particular R and R' are X and A as defined herein and R" may be an alkyl, alkenyl, alkynyl, aryl, heteroaryl, carbocyclic, or heterocyclic group.

The term "thioether" as used herein refers to a group of the formula R—S—R' wherein R and R' are carbon containing groups bonded to sulfur through a carbon atom. In particular R and R' are X and A as defined herein.

The term "amide" as used herein refers to a group of the formula RC(=O)NR'R" wherein R, R' and R" are either hydrogen or carbon containing groups bonded to carbon or nitrogen through a carbon atom, typically R, R' and R" are hydrogen or selected from unsubstituted or substituted alkyl, alkenyl, alkynl, alkylene, alkenylene and aryl groups. In particular, one of R and R' is X and the other is A as defined herein, and R" is hydrogen or a $C_1$ to $C_6$ alkyl group.

The term "cholesteryl" as used herein refers to the group depicted below

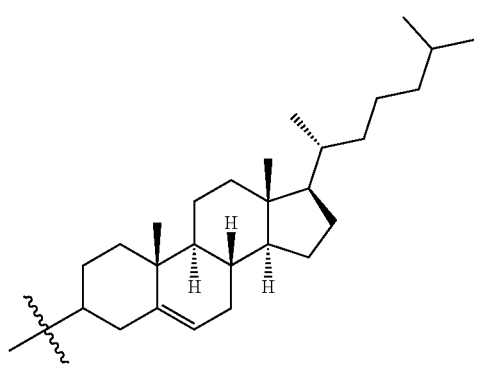

Cholesteryl group

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C$=O)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, typically $^1H$. Similarly, by way of example, each individual carbon atom present in formula (I), or in the formulae depicted hereinafter, may be present as a $^{12}C$, $^{13}C$ or $^{14}C$ atom, typically $^{12}C$.

In one embodiment of the invention, A is —$R^{10}CH(OR^{12})R^{11}CH(OR^{13})Z$, wherein $R^{12}$ and $R^{13}$ are the same or different and each is a $C_{10}$ to $C_{24}$ alkyl or alkenyl group, $R^{10}$ and $R^{11}$ are the same or different and each is a covalent bond or a —$(CH_2)_s$— group wherein s is 1, 2 or 3, Z is a hydrogen atom or a $C_1$ to $C_3$ alkyl group. Suitably $R^{12}$ and $R^{13}$ are $C_{12}$ to $C_{22}$, more suitably $C_{14}$ to $C_{20}$, still more suitably $C_{16}$ to $C_{18}$ alkyl or alkenyl groups. Typically A is —$CH_2CH(OR^{12})CH_2OR^{13}$, specifically (R)-2,3-di(octadecyloxy)propyl. In another embodiment, A is an unsubstituted or substituted $C_{17}$ to $C_{35}$ group comprising the fused ring system of a steroid, typically is an unsubstituted or substituted $C_{17}$ to $C_{28}$ group comprising the fused ring system of a steroid, more typically A is a steroidal group, even more typically A is cholesteryl.

Ar is an aryl group. Typically Ar is a naphthyl or phenyl group. More typically Ar is a phenyl group.

Typically the group Ar is substituted by at least one group $R^3$ which is of the formula —$YC(R^4)(R^5)CO_2R^6$ and is the same or different to the group $R^2$. More typically Ar is substituted by one group $R^3$ which is of the formula —$YC(R^4)(R^5)CO_2R^6$ and is the same or different to the group $R^2$. Even more typically Ar is substituted by one group $R^3$ which is of the formula —$YC(R^4)(R^5)CO_2R^6$ and is the same as the group $R^2$. More typically still Ar is substituted by one group $R^3$ which is of the formula —$CH_2C(CH_3)_2CO_2CH_3$ or —$CH_2C(CH_3)_2CO_2H$ and is the same as the group $R^2$.

Typically the compounds of the invention have the structure of formula (II)

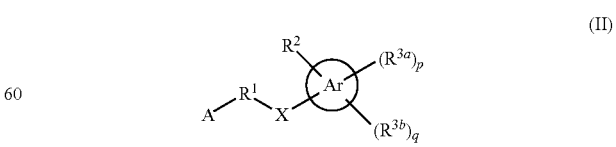

(II)

wherein Ar, A, X, $R^1$ and $R^2$ are as defined above. $R^{3a}$ is of the formula —$YC(R^4)(R^5)CO_2R^6$ and is the same or different to the group $R^2$, and each $R^{3b}$ is the same or different and each is selected from a halogen atom, a $C_1$ to $C_6$ alkyl group, a $C_1$ to $C_6$ alkenyl group, a $C_1$ to $C_6$ alkynl group or a $C_1$ to $C_6$ alkoxy group. Y, $R^4$, $R^5$ and $R^6$ are as defined above. p and q are each an integer from 0 to 6, typically each is an integer from 0 to 3, more typically each is 0 or 1, even more typically p is 1 and q is 0. More typically $R^{3a}$ is the same as $R^2$. Even more typically $R^{3a}$ is the same as $R^2$ and all $R^{3b}$ are the same. More typically still $R^{3a}$ is the same as $R^2$ and all $R^{3b}$ are hydrogen. Most typically, $R^{3a}$ is the same as $R^2$ and is —$CH_2C(CH_3)_2CO_2CH_3$ or —$CH_2C(CH_3)_2CO_2H$, and all $R^{3b}$ are hydrogen.

Typically the compounds of the invention have the structure of formula (III)

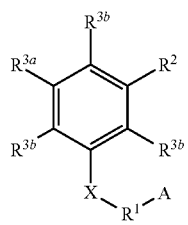

(III)

wherein A, X, $R^1$, $R^2$ and $R^{3a}$ are as defined above. $R^{3b}$ is as defined above with the additional option of being a hydrogen atom. More typically $R^{3a}$ is the same as $R^2$. Even more typically $R^{3a}$ is the same as $R^2$ and all $R^{3b}$ are the same. More typically still $R^{3a}$ is the same as $R^2$ and all $R^{3b}$ are hydrogen. Most typically, $R^{3a}$ is the same as $R^2$ and is —$CH_2C(CH_3)_2CO_2CH_3$ or —$CH_2C(CH_3)_2CO_2H$, and all $R^{3b}$ are hydrogen.

$R^1$ is a phosphodiester, phosphotriester, thioether or amide group. Wherein $R^1$ is an amide it may be of the form XC(=O)NRA or AC(=O)NRX, where R is a hydrogen or carbon containing organic group, typically R is hydrogen or $C_1$ to $C_6$ alkyl, more typically R is hydrogen. Typically $R^1$ is a phosphodiester or phosphotriester group. More typically $R^1$ is a phosphodiester group.

Typically, Y is —$(CH_2)_m$— wherein m is 1, 2 or 3. More typically Y is —$CH_2$—.

Typically $R^4$ and $R^5$ are the same or different and each is a $C_1$ to $C_6$ alkyl group, optionally a $C_1$ to $C_3$ alkyl group. More typically $R^4$ and $R^5$ are the same and each is a $C_1$ to $C_6$ alkyl group. Even more typically $R^4$ and $R^5$ are the same and each is a $C_1$ to $C_3$ alkyl group. More typically still $R^4$ and $R^5$ are both a methyl group.

Typically $R^6$ is a hydrogen atom or a $C_1$ to $C_3$ alkyl group. More typically $R^6$ is a hydrogen atom or a methyl group.

Typically X is a straight chain or branched unsubstituted or substituted $C_8$ to $C_{20}$ alkylene or alkenylene group, which is optionally interrupted by one or more —$NR^9$—, —O— or —S— linkages, wherein $R^9$ is a $C_1$ to $C_6$ alkyl group. More typically X is a straight chain or branched unsubstituted or substituted $C_8$ to $C_{20}$ alkylene or alkenylene group, which is optionally interrupted by one, two or three non-adjacent —$NR^9$—, —O— or —S— linkages. Even more typically X is a straight chain or branched $C_8$ to $C_{20}$ alkylene or alkenylene group, for example a $C_{10}$ to $C_{20}$, $C_{10}$ to $C_{18}$ or $C_{11}$ to $C_{17}$ alkylene or alkenylene group. More typically still X is a straight chain $C_8$ to $C_{20}$ alkylene or alkenylene group, for example a $C_{10}$ to $C_{20}$, $C_{10}$ to $C_{18}$ or $C_{11}$ to $C_{17}$ alkylene or alkenylene group.

Specific novel compounds in accordance with the present invention include:

Compound 1: dimethyl 3,3'-(5-(11-(((2-chlorophenoxy)(((3R,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)phosphoryl)oxy)undecyl)-1,3-phenylene)bis(2,2-dimethylpropanoate);

Compound 2: 3,3'-(5-(11-(((((3R,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)(hydroxy)phosphoryl)oxy)undecyl)-1,3-phenylene)bis(2,2-dimethylpropanoic acid), ammonium salt;

Compound 3: dimethyl 3,3'-(5-(11-((((S)-2,3-bis(octadecyloxy)propoxy)(2-chlorophenoxy)phosphoryl)oxy)undecyl)-1,3-phenylene)bis(2,2-dimethylpropanoate);

Compound 4: 3,3'-(5-(11-((((S)-2,3-bis(octadecyloxy)propoxy)(hydroxy)phosphoryl)oxy)undecyl)-1,3-phenylene)bis(2,2-dimethylpropanoic acid), ammonium salt;

Compound 5: dimethyl 3,3'-(5-(17-(((2-chlorophenoxy)(((3R,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)phosphoryl)oxy)heptadecyl)-1,3-phenylene)bis(2,2-dimethylpropanoate);

Compound 6: 3,3'-(5-(17-(((((3R,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)(hydroxy)phosphoryl)oxy)heptadecyl)-1,3-phenylene)bis(2,2-dimethylpropanoic acid), ammonium salt.

Compounds of formula (I) can be prepared using standard techniques and reagents known to those skilled in the art, such as those described below and in the Examples.

Compounds Wherein $R^1$ is a Phosphodiester or Phosphotriester

Compounds of formula (I) in which $R^1$ represents a phosphodiester may be prepared by the skilled person from the corresponding compounds in which $R^1$ represents a phosphotriester, using standard reactions known from the art, such as hydrolysis.

Compounds of formula (I) in which $R^6$ represents a hydrogen atom may be prepared by the skilled person from the corresponding esters in which $R^6$ represents an unsubstituted or substituted alkyl group, using standard reactions known from the art, such as hydrolysis.

Compounds of formula (I) in which $R^1$ is a phosphotriester group and $R^6$ is an unsubstituted or substituted alkyl may be prepared from compounds of formula (IV):

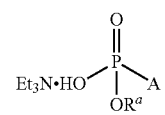

(IV)

wherein A is as defined above and $R^a$ is an alkyl, alkenyl, alkynyl, aryl, heteroaryl, carbocyclic, or heterocyclic group; by reaction with an activating agent to generate a leaving group from the hydroxyl, followed by reaction with a compound of formula (V):

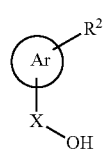

(V)

wherein Ar, X and $R^2$ are as defined above.

Compounds of formula (IV) may be prepared by reacting a compound of formula (VI)

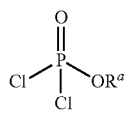
(VI)

wherein $R^a$ is as defined above; with a compound of formula A-OH, wherein A is as defined above, and a base. Compounds of formula A-OH may be purchased commercially or be readily synthesised by the skilled person.

Compounds of formula (V) may be prepared from a compound of formula (VII)

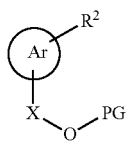
(VII)

wherein Ar, $R^2$ and X are as defined above and PG refers to a protecting group for an alcohol; for example, if PG refers to —$CPh_3$, where Ph is a phenyl ring, the deprotection can be done by reaction with triisopropylsilane and concentrated hydrochloric acid.

Compounds of formula (VII) may be prepared by a cross coupling reaction, for example the Suzuki reaction, between a compound of formula (VIII)

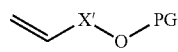
(VIII)

wherein X' refers to the group required to give a group X as defined above in the compound of formula (VII) and PG is as defined above; and a compound of formula (IX)

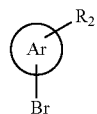
(IX)

wherein Ar and $R^2$ are as defined above. For example, the compound of formula (VIII) may be reacted with 9-borabi-cyclo[3.3.1]nonane. The resulting product can be reacted with the compound of formula (IX) together with tetrakis(triphenylphosphine)palladium(O), potassium carbonate and dimethylformamide.

Compounds of formula (VIII) may be prepared by the reaction of a compound of formula (X)

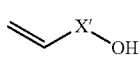
(X)

wherein X' is as defined above; using standard techniques known to those skilled in the art. For example, if PG refers to —$CPh_3$ this can be done by reaction with base followed by triphenylmethyl chloride. Compounds of formula (X) may be purchased commercially, or be readily synthesised by the skilled person from commercially available compounds.

Compounds of formula (IX) may be synthesised from the reaction of a compound of formula (XI)

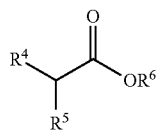
(XI)

wherein $R^4$, $R^5$ and $R^6$ are as defined above; with a base followed by a compound of the formula (XII)

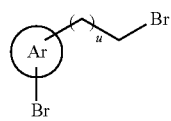
(XII)

wherein Ar is as defined above and u is an integer from 0 to 2.

Compounds of the formula (XII) may be synthesised by the reaction of a compound of formula (XIII)

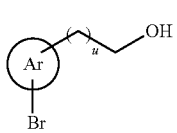
(XIII)

wherein Ar and u are as defined above; with a brominating agent. Compounds of formula (XIII) may be purchased commercially or be readily synthesised by the skilled person.

Compounds Wherein $R^1$ is a Thioether

Compounds of formula (I) wherein $R^1$ is a thioether may be prepared from a compound of formula (XIV)

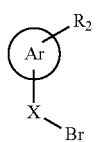
(XIV)

wherein Ar, X and $R^2$ are as defined above; by reaction with a compound of formula A-SH, wherein A is as defined above, and a base.

Compounds of formula (XIV) may be synthesised from compounds of formula (V) by reaction with a brominating agent or mixture, for example tetrabromomethane and triphenylphosphine.

The compounds of formula A-SH above may be synthesised from a compound of formula A-OH by reaction with hydrogen sulfide.

Compounds Wherein $R^1$ is an Amide

Compounds of formula (I) wherein $R^1$ is an amide may have amide groups of formula $XC(=O)NR^{14}A$ (see formula (XV)) or $AC(=O)NR^{14}X$ (see formula (XVI)).

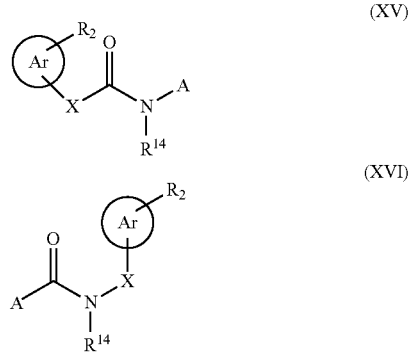

wherein Ar, $R^2$, X and A are as defined above and $R^{14}$ is an hydrogen atom or alkyl, alkenyl, alkynyl, aryl, heteroaryl, carbocyclic, or heterocyclic group.

An example of suitable disconnections for a compound of formula (XV) is shown in scheme 1 below. Analogous disconnections may be done for a compound of formula (XVI).

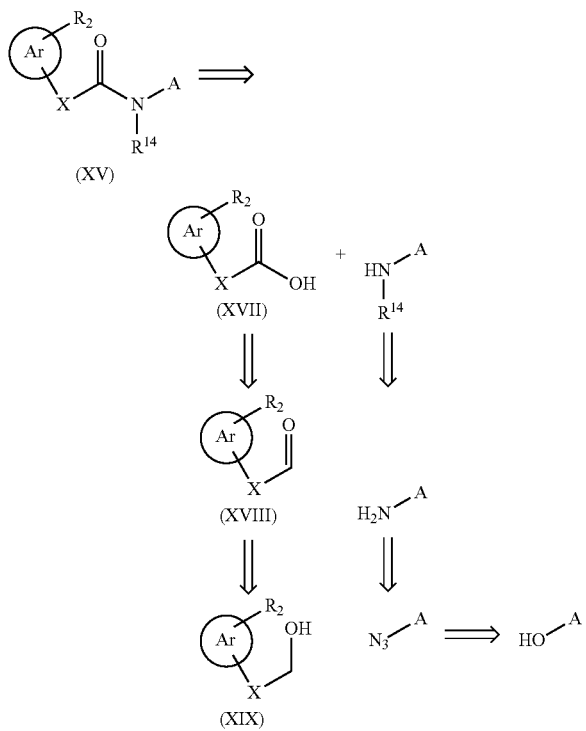

Scheme 1

A synthetic route based on the above disconnections is described below.

Compounds of formula (XV) may be prepared from a condensation reaction between a compound of formula (XVII); and a compound of formula $A$-$NHR^{14}$ wherein A and $R^{14}$ are as defined above.

Compounds of formula (XVII) may be synthesised from a compound of formula (XVIII), by oxidation with many reagents known in the art, for example silver (I) oxide.

Compounds of formula (XVIII) may be synthesised from a compound of the formula (XIX). For example a compound of the formula (XIX) may be oxidised by the Swern oxidation to give a compound of the formula (XVIII).

Compounds of formula (XIX) and (XVIII) may be synthesised from a compound of formula (V) above by reactions known from the art. For example, by activation of the hydroxyl group followed by an umpolung reaction with a 1,3-dithiane derived from formaldehyde, and finally oxidation of the product to either the alcohol or aldehyde.

Compounds of the formula $A$-$NHR^{14}$ wherein $R^{14}$ is not hydrogen may be synthesised from a compound of the formula $A$-$NH_2$, by reaction with an alkylating agent or the like, controlled to ensure mono-substitution.

Compounds of the formula $A$-$NH_2$ may be synthesised from a compound of the formula $A$-$N_3$, for example by reduction with triphenylphosphine and water in tetrahydrofuran.

Compounds of the formula $A$-$N_3$ may be synthesised from a compound of the formula $A$-$OH$ above, for example by the Mitsonobu reaction using hydrazoic acid to yield the azide.

Compounds of formula (XVI) may be prepared by an analogous procedure to compounds of formula (XV) using standard techniques well known in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

It has been shown that the compounds of the present invention are effective transfection enhancing agents via their endosomolytic properties. Thus, the compounds of the present invention are designed to incorporate into the membrane of liposomes, the compound-liposome complex in turn associating with plasmid DNA. The compounds of the present invention are therefore useful in gene therapy i.e. the delivery of transgenic oligonucleotides to a cell. Transgenic oligonucleotides include genes coding for therapeutic proteins (DNA), RNAs and also nucleic acids involved in gene silencing, such as siRNAs or antisense RNAs.

The compounds of the present invention may additionally be used in the delivery of proteins/peptides.

The compounds of the invention may be used in conjunction with any appropriate method for delivery of transgenic oligonucleotides/polynucleotides or proteins/peptides.

Transgenic oligonucleotides (or proteins/peptides) may be delivered to cells using the compounds of the invention in vitro. However, in the context of the present invention the transgenic oligonucleotides (or proteins/peptides) are typically delivered to cells in vivo. The compounds of the invention may also be used in delivery of a transgenic oligonucleotide (or protein/peptide) to cells in vitro, before implantation of the cells in vivo into a subject. Such techniques are well known in the art.

The majority of gene therapy trials in patients to date have been performed using viral vectors. Viral vectors include retroviruses, adenoviruses, or adeno-associated viruses. The compounds of the invention are though typically used in non-viral methods for delivery, which are easier to handle and associated with fewer safety concerns. The simplest non-viral delivery system is the use of naked oligonucleotides/polynucleotides (preferably plasmid DNA). The compounds of the invention may be used in conjunction with naked oligonucleotides/polynucleotides. Oligonucleotides/polynucleotides may also be delivered within e.g. a liposome (a lipoplex), a polymersome, a polyplex, a lipopolyplex, or associated with dendrimers. Furthermore, inorganic nanoparticles and cell penetrating peptides may be used. Such techniques are well known in the art.

In the context of the present invention, a "gene therapy vector" refers to any element encompassing a transgenic oligonucleotide/polynucleotide that is to be delivered to a cell. For example, the transgenic oligonucleotide/polynucleotide may be present within a plasmid vector (for naked DNA), which typically contains control elements for expressing the oligonucleotide/polynucleotide once inside the target cell. Lipoplexes, polyplexes, lipopolyplexes etc may also be seen as gene therapy vectors. A polyplex refers to a complex of a polymer (e.g. a condensing agent such as PEI) with a transgenic oligonucleotide/polynucleotide. A lipoplex refers to a complex of lipids and a transgenic oligonucleotide/polynucleotide. The lipids may take the form e.g. of a liposome or a micelle. The term lipopolyplex refers to a complex of a polymer (e.g. condensing agent), transgenic oligonucleotide/polynucleotide and lipid. Methods of forming polyplexes, lipoplexes and lipopolyplexes are well known in the art.

The compounds of the invention are typically used in lipoplexes/lipopolyplexes either in conjunction with, or as part of, liposomes in delivery of a transgenic material to a target cell.

Where the compounds of the invention are administered in conjunction with, or as part of, a lipoplex, or a lipopolyplex (e.g. a liposome), the amount of the compound of the invention, relative to the amount of lipid (for example as determined by scintillation counting) may be from 1 to 50 mol %. Typically the amount of the compound of the invention is from 5 to 50 mol %, more typically from 10 to 50 mol %, even more typically from 20 to 50 mol %, more typically still from 20 to 40 mol %, most typically about 20 mol %. The lipid may any lipid known to be suitable for use in lipoplexes or lipopolyplexes (typically for use in liposomes or micelles). Lipids known to be useful in this regard include phospholipids and sterols. Particularly useful lipids include phosphatidylcholines, phosphatidylglycerols, phosphatidylethanolamines, PEG phospholipids, cholesterol derivatives and bola amphiphiles. In particular the lipid may be dioleoylphosphatidylcholine (DOPC), dioleoylphosphatidylethanolamine (DOPE), dioleoylphosphatidylserine, or a salt thereof (DOPS), cholesteryl hemisuccinate (CHEMS), cholesterol or oleic acid, or any combination thereof. The molar ratio of lipid:nucleic acid phosphate content may be from 0.1:1 to 40:1. Typically the ratio will be from 0.1:1 to 36:1, more typically from 0.4:1 to 20:1, more typically from 0.4:1 to 12:1, even more typically from 0.6:1 to 5:1, more typically still from 0.6:1 to 2:1, most typically from 0.8:1 to 2:1

For example, the amount of compound relative to the total amount of lipid may be 20-40 mol % and the molar ratio of total lipid to DNA may be between 2:1 and 5:1.

The present invention also provides a pharmaceutical composition which comprises a compound in accordance with the invention as described above, or a pharmaceutically acceptable salt or solvate thereof, in association with one or more pharmaceutically acceptable carriers. In one embodiment the composition may further comprise a gene therapy vector.

Pharmaceutical compositions according to the invention may take a form suitable for parenteral, intravenous, oral, buccal, nasal, topical, ophthalmic or rectal administration, or a form suitable for administration by inhalation or insufflation. In a particular embodiment the compounds will be suitable for parenteral administration.

In some embodiments, for example when using naked oligonucleotides, the pharmaceutical composition is formulated for direct administration to the desired tissue. For example, the pharmaceutical composition comprising the compound(s) of the invention and e.g. the naked oligonucleotide may be applied by injection intravenously, directly to muscle, to the site of a tumour or to the skin.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the composition may be in powder form for constitution with a suitable vehicle, e.g. sterile pyrogen-free water, before use.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate.

Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral administration, and from around 10 ng/kg to 50 mg/kg body weight for parenteral administration.

The compound of the invention may be administered simultaneously, separately, or sequentially with a gene therapy vector encompassing a transgenic oligonucleotide. For example, the gene therapy vector may be present in the same pharmaceutical composition as the compound of the invention. Alternatively, the gene therapy vector and the compound of the invention may be present in separate pharmaceutical compositions. Where the gene therapy vector and the compound of the invention are in separate compositions they may, in one embodiment, be administered simultaneously (i.e. at the same time). Alternatively the gene therapy vector and the compound of the invention may be administered sequentially (i.e. the compound of the invention is administered immediately before or after the gene therapy vector). In yet a further embodiment the gene therapy vector and the compound of the invention may be administered separately (i.e. the compound of the invention is administered before or after the gene therapy vector for example at a time interval from 2 minutes to 2 hours, more specifically 5 minutes to 1 hour or even more specifically 10 minutes to 30 minutes).

The compounds in accordance with the present invention are beneficial when used in conjunction with a gene therapy vector in the treatment and/or prevention of various human ailments, including oncological disorders and genetic disorders.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

The most prevalent genetic disorders include Angelman syndrome, Canavan disease, Charcot-Marie-Tooth disease, colour blindness, cri du chat, cystic fibrosis, Down syndrome, Duchenne muscular dystrophy, haemochromatosis, haemophilia, Klinefelter syndrome, neurofibromatosis, phenylketonuria, polycystic kidney disease, Prader-Willi syndrome, sickle cell disease, spinal muscular atrophy, Tay-Sachs disease, Turner syndrome and 22q 1.2 deletion syndrome. The compounds in accordance with the invention are adapted to function as a key component in gene replacement therapy and are therefore effective in the treatment of genetic disorders.

The present invention is explained in more detail in the following by referring to Examples, which are not to be construed as limitative.

EXAMPLES

Reference Example 1

2-Chlorophenyl 3-O-Cholesteryl Phosphate, Triethylammonium Salt

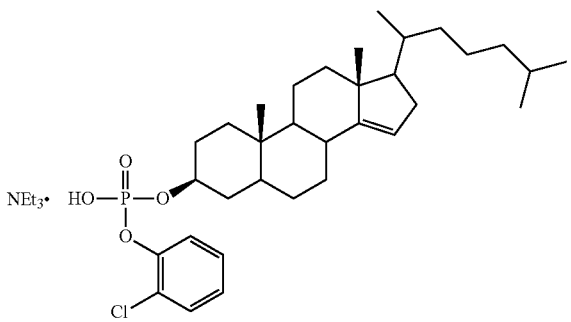 [SMILES: CC(C)CCCC(C)C1CC=C2C3CCC4C[C@@H](OP(=O)(O)Oc5ccccc5Cl)CC[C@]4(C)C3CC[C@@]21C]

1,2,4-Triazole (2.76 g, 40.0 mmol) was dissolved in anhydrous tetrahydrofuran (100 ml), and to the vigorously stirring solution was added triethylamine (4.90 ml, 3.56 g, 35.2 mmol) followed dropwise by 2-chlorophenylphosphodichloridate (2.40 ml, 3.65 g, 14.9 mmol) and the reaction mixture stirred at ambient temperature for 40 min. The copious white precipitate of triethylammonium chloride was removed by filtration and to the resultant clear, colourless supernatant was added cholesterol (3.88 g, 10.0 mmol), and the reaction mixture stirred at ambient temperature for a further 4 hr. The reaction mixture was poured into triethylammonium bicarbonate solution (1M, 200 ml) and extracted into dichloromethane (200 ml). The organic phase was washed with further triethylammonium bicarbonate solution (2×200 ml) and dried over anhydrous sodium sulphate, then solvent was removed in vacuo to a white, amorphous solid. This was triturated with diisopropyl either to yield the title compound (5.18 g, 7.64 mmol) as a white, crystalline solid.

$\delta^1$H (CDCl$_3$): 7.71 (d, 1H, ClPh.C$^3$—$\underline{H}$); 7.31 (d, 1H, ClPh.C$^6$—$\underline{H}$); 7.18 (6, 1H, ClPh.C$^4$—$\underline{H}$); 6.93 (t, 1H, ClPh.C$^5$—$\underline{H}$); 5.30 (m, 1H, Chol.C$^6$—$\underline{H}$); 4.17 (bm, 1H, —O$_3$PO-Chol.C$^3$—$\underline{H}$); 3.05 (bm, 6H, N(C$\underline{H}_2$CH$_3$)$_3$); 2.42-

2.33 and 1.97-1.76 (2×bm, 3H and 5H, Chol.C$^{1,2,4,7}$—$\underline{H}$); 1.31 (t, 9H, N(CH$_2$C$\underline{H}_3$)$_3$;); 1.57-1.00 (bm, 22H, Chol. C$^{alicyclic}$—$\underline{H}$ and Chol.C$^{aliphatic}$—$\underline{H}$); 0.97 (s, 3H, C$^{19}$—$\underline{H}_3$); 0.91 (d, 3H, Chol.C$^{21}$—$\underline{H}$); 0.86 (d, 6H, Chol.C$^{24,25}$—$\underline{H}_3$); 0.66 (s, 3H, Chol.C$^{18}$—$\underline{H}_3$). C$_{39}$H$_{65}$ClO$_4$PN requires: C=69.05%, H=9.66%; found: C=68.90%, H=9.70%. m/z (ES+): 678 (MNEt$_3^+$, 60%); 779 (M(NEt$_3$)$_2^+$, 100%). mp.=138° C. (dec.) (uncorrected).

Reference Example 2

2-Chlorophenyl (R)-2,3-Di(octadecyloxy)propyl Phosphate, triethylammonium Salt

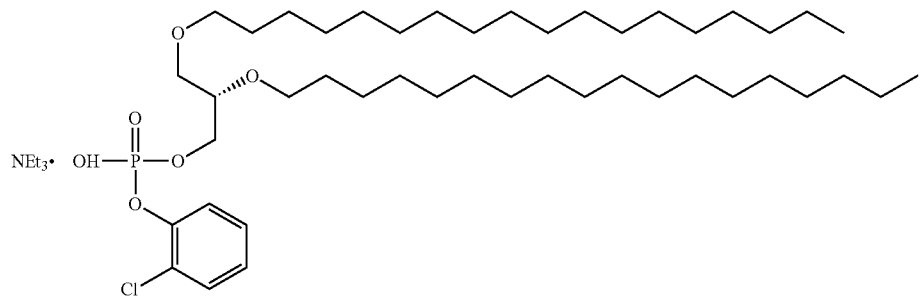 [SMILES: "NEt3·" ; CCCCCCCCCCCCCCCCCCOC[C@@H](COP(=O)(O)Oc1ccccc1Cl)OCCCCCCCCCCCCCCCCCC]

1,2,4-Triazole (1.56 g, 22.6 mmol) was dissolved in anhydrous tetrahydrofuran (50 ml), and to the vigorously stirring solution was added triethylamine (2.85 ml, 2.08 g, 20.6 mmol) followed dropwise by 2-chlorophenylphosphodichloridate (1.37 ml, 2.07 g, 8.43 mmol) and the reaction mixture stirred at ambient temperature for 1 hr. The copious white precipitate of triethylammonium chloride was removed by filtration and to the resultant clear, colourless supernatant was added 1,2-O-dioctadecyl-S$_n$-glycerol (2.50 g, 4.19 mmol) dissolved in anhydrous tetrahydrofuran (10 ml), and the reaction mixture stirred at ambient temperature overnight. The reaction mixture was poured into deionised water (100 ml) and shaken vigorously to a homogeneous emulsion, then stood at ambient temperature for 30 min. The emulsion was extracted into dichloromethane (100 ml), and the organic phase was washed with triethylammonium bicarbonate solution (100 ml) and dried over anhydrous sodium sulphate, then solvent was removed in vacuo and solid residue evaporated from diethyl ether (100 ml) to a white, waxy, amorphous solid. Crude product was purified on silica (6%, methanol/1% triethylamine/dichloromethane) to yield the title compound (2.88 g, 3.24 mmol) as a fine white solid.

$\delta^1$H (CDCl$_3$): 7.53 (d, 1H, ClPh.C$^3$—$\underline{H}$); 7.28 (d, 1H, ClPh.C$^6$—$\underline{H}$); 7.12 (t, 1H, ClPh.C$^4$—$\underline{H}$); 6.92 (t, 1H, ClPh.C$^5$—$\underline{H}$); 3.83 (s, 2H, —O$_3$POC$\underline{H}_2$—); 3.50-3.37 (bm, 4H, 2×—OC$\underline{H}_2$—); 3.33-3.26 (bm, 3H, —OC$\underline{H}$< and —O$_3$POC$\underline{H}_2$—); 3.07 (bm, 6H—), NC$\underline{H}_2$CH$_3$)$_3$); 1.42 (bm, 4H, 2×—C$\underline{H}_2$CH$_2$O—); 1.20-1.15 (bm, 69H(-), N(CH$_2$C$\underline{H}_3$)$_3$ and 2×—(C$\underline{H}_2$)$_{15}$—); 0.80 (t, 6H, 2×—O(CH$_2$)$_{17}$C$\underline{H}_3$). C$_{45}$H$_{84}$O$_6$ClP.C$_6$H$_{15}$N requires: C=68.92%, H=11.23%, N=1.58%; found: C=66.11%, H=10.53%, N=0.41%. m/z (ES+): 88.8 (MNEt$_3^+$, 100%); 809.7 (MNa$^+$, 45%). mp.=54-56° C. (uncorrected).

Reference Example 3

1,3-(5-Bromobenzene)-bis-methanol

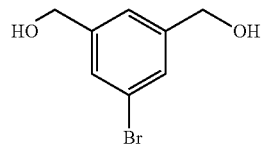 [SMILES: OCc1cc(Br)cc(CO)c1]

To a vigorously stirred suspension of lithium aluminium hydride (7.2 g, 190 mmol) in anhydrous tetrahydrofuran (500 ml), maintained at ~0° C. in an ice bath, was added dropwise a solution of dimethyl 5-bromoisophthalate (23.6 g, 86.5 mmol) in anhydrous tetrahydrofuran (100 ml) over 2 hr, and the reaction mixture then allowed to attain ambient temperature while stirring vigorously overnight. To this was then added dropwise, deionised water (7.2 ml) followed by sodium hydroxide solution (3M, 7.2 ml) followed by further deionised water (21.6 ml). The pale grey precipitate was removed from the clear, colourless supernatant by filtration and solvent removed in vacuo to yield the title compound (15.3 g, 70.6 mmol) as a white, crystalline solid.

$\delta^1$H (d$_6$-DMSO): 6.96 (s, 2H, Arom.C$^{4,6}$—$\underline{H}$); 6.81 (s, 1H, Arom.C$^2$—$\underline{H}$); 4.14 (s, 4H, 2×—C$\underline{H}_2$OH). C$_8$H$_7$O$_2$Br requires: C=44.27%, H=4.18%; found: C=44.81%, H=4.26%. m/z (EI+): 216/218 (M$^+$, 15%). mp.=88-90° C. (uncorrected).

Reference Example 4

5-Bromo-1,3 bis(bromomethyl)benzene

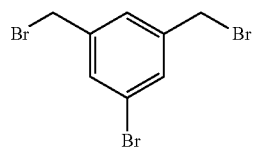

To 1,3-(5-bromobenzene)-bis-methanol (31.5 g, 145 mmol) in anhydrous dichloromethane (500 ml) was added tetrabromomethane (103.0 g, 311 mmol), followed dropwise by a solution of triphenylphosphine (81.5 g, 311 mmol) in anhydrous dichloromethane (150 ml), and the reaction mixture stirred at ambient temperature overnight. Solvent was removed in vacuo to a clear, dark red-brown, viscous oil which was redissolved in dichloromethane (500 ml) and added dropwise to vigorously stirring, ice cold diethyl ether (1.51). The precipitate of triphenylphosphine oxide was removed by filtration and solvent was removed in vacuo from the resultant clear supernatant to give a finely crystalline slurry. Crude product was purified on silica (dichloromethane) to a pale yellow crystalline solid which was recrystallised from dichloronmethane/hexane, 1:2 to yield the title compound (30.0 g, 87.5 mmol) as large colourless, needle-like crystals.

$\delta^1$H (CDCl$_3$): 7.47 (s, 2H, Arom.C$^{4,6}$—$\underline{H}$); 7.34 (s, 1H, Arom.C$^2$—$\underline{H}$); 4.40 (s, 4H, 2×—C$\underline{H}_2$Br). m/z (CI): 340/342/344/346 (M$^+$, 10%); 278/280/282 (MNH$_4^+$—Br, 100%); 261/263/265 (M$^+$-Br, 50%). C$_8$H$_7$Br$_3$ requires: C=28.03%, H=2.06%; found: C=28.21%, H=2.00%. mp.=94-96° C. (uncorrected).

Reference Example 5

Dimethyl 1,3-(5-Bromobenzene)-bis(2,2-dimethylpropanoate)

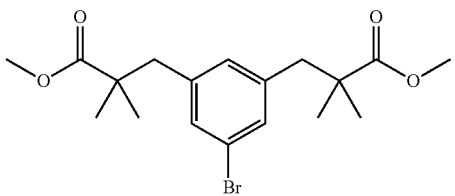

To methyl isobutyrate (7.35 ml, 6.55 g, 64.1 mmol) dissolved in anhydrous tetrahydrofuran (100 ml) and stirred at −78° C. in a dry ice/acetone bath, was added dropwise lithium diisopropylamide solution in heptane/ethylbenzene/tetrahydrofuran (2M, 35.3 ml, 70.6 mmol). The reaction mixture was stirred at −78° C. for 2 hr then a solution of 5-romo-1,3-bis(bromomethyl)benzene (10.0 g, 29.2 mmol) in anhydrous tetrahydrofuran (15 ml) was added dropwise. The reaction mixture was stirred at −78° C. for a further 2 hr then allowed to attain ambient temperature while stirring overnight. Solvent was removed in vacuo and the resultant yellow slurry was poured into saturated ammonium chloride solution (200 ml) and extracted into dichloromethane (200 ml). The organic layer was washed with deionised water (200 ml) then brine (200 ml) and dried over anhydrous magnesium sulphate, and solvent removed in vacuo to a yellow crystalline solid. The crude product was recrystallised from hot isopropyl ether (first crop, 200 ml; second crop, 50 ml) to yield the title compound (8.73 g, 22.7 mmol) as fine colourless needles.

$\delta^1$H (CDCl$_3$): 7.10 (s, 2H, Arom.C$^{4,6}$—$\underline{H}$); 6.77 (s, 1H, Arom.C$^2$—$\underline{H}$); 3.66 (s, 6H—CO$_2$C$\underline{H}_3$); 2.77 (s, 4H, Arom.C$^{1,3}$C$\underline{H}_2$—); 1.16 (s, 12H, 2×—C(C$\underline{H}_3$)$_2$CO$_2$—). C$_{18}$H$_{25}$O$_4$Br requires: C=56.11%, H=6.54%; found: C=56.23%, H=6.58%. m/z (ES+): 407/409 (MNa$^+$, 100%). mp.=127-129° (uncorrected).

Reference Example 6

1-Triphenylmethoxy-10-undecene

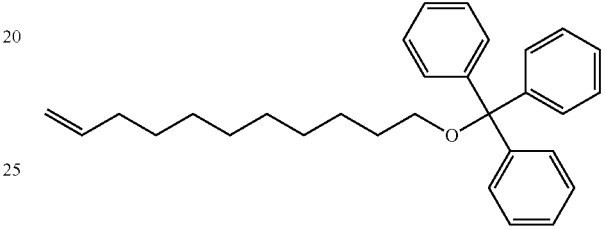

To undec-10-en-1-ol (10.07 g, 59.13 mmol) dissolved in anhydrous dichloromethane (300 ml) was added anhydrous triethylamine (9.10 ml, 6.61 g, 65.3 mmol) then portionwise with stirring, triphenylmethyl chloride (17.33 g, 62.16 mmol), and the reaction mixture stirred at ambient temperature overnight. Crystalline triethylammonium chloride was removed by filtration and solvent was removed in vacuo to give an orange-brown viscous oil. Crude product was purified on silica (hexane) to yield the title compound (21.96 g, 53.22 mmol) as a clear, colourless, viscous oil.

$\delta^1$H (CDCl$_3$): 7.48-7.44 and 7.33-7.21 (2×bm, 6H and 9H, C$^{trityl}$—$\underline{H}$); 5.90-5.76 (bm, 1H, —C$\underline{H}$=CH$_2$); 5.04-4.92 (bm, 2H, —CH=C$\underline{H}_2$); 3.06 (t, 2H, —C$\underline{H}_2$OCPh$_3$); 2.09-2.02 (bm, 2H, —C$\underline{H}_2$CH$_2$OCPh$_3$); 1.68-1.58 (bm, 2H, —C$\underline{H}_2$CH=CH$_2$); 1.41-1.23 (bm, 12H, —(C$\underline{H}_2$)$_6$—). C$_{30}$H$_{36}$O requires: C=87.33%, H=8.80%; found: C=87.35%, H=8.78%. m/z (EI+): 412.4 (M$^+$, 2%); 335.3 ((M−Ph)$^+$, 2%).

Reference Example 7

Dimethyl 1,3-[5-(Triphenylmethoxyundecyl)benzene]-bis(2,2-dimethylpropanoate

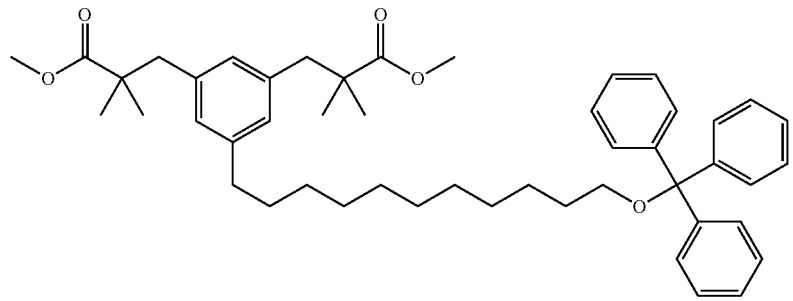 [SMILES: COC(=O)C(C)(C)Cc1cc(CCCCCCCCCCCOC(c2ccccc2)(c2ccccc2)c2ccccc2)cc(CC(C)(C)C(=O)OC)c1]

To 1-triphenylmethoxy-10-undecene (2.75 g, 6.66 mmol) dissolved in anhydrous tetrahydrofuran (60 ml) and stirred at ~0° C. in an ice bath, was added dropwise a solution of 9-borabicyclo[3.3.1]nonane in tetrahydrofuran (0.5M, 16.0 ml, 8.0 mmol). The reaction mixture was stirred at ~0° C. for 2.5 hr then dimethyl 1,3-(5-bromobenzene)-bis(dimethylpropanoate) (3.00 g, 7.79 mmol) was added together with tetrakis(triphenylphosphine)palladium(0) (0.61 g, 0.53 mmol), anhydrous potassium carbonate (2.60 g) and anhydrous dimethylformamide (20 ml) and the reaction mixture refluxed at 85° C. under an argon atmosphere overnight. The reaction mixture was then poured into saturated ammonium chloride solution (200 ml) and extracted into ethyl acetate (200 ml). The organic phase was washed with deionised water (200 ml) then brine (200 ml) and dried over anhydrous sodium sulphate. Solvent was removed in vacuo to a clear, yellowish viscous oil, and the crude product purified on silica (10% to 20% diethyl ether/hexane) to yield the title compound (2.67 g, 3.71 mmol) as a clear, colourless, viscous oil which solidified to a white, waxy solid on standing.

$\delta^1$H (CDCl$_3$): 7.46-7.42 and 7.31-7.19 (2×bm, 5H and 10H, C$^{trityl}$—$\underline{H}$); 6.75 (s, 2H, Arom.C$^{4,6}$—$\underline{H}$); 6.65 (s, 1H, Arom.C$^2$—$\underline{H}$); 3.65 (s, 6H, 2×—CO$_2$C$\underline{H}_3$); 3.04 (t, 2H, —C$\underline{H}_2$OCPh$_3$); 2.78 (s, 4H, Arom.C$^{1,3}$C$\underline{H}_2$—); 2.50 (t, 2H, —C$\underline{H}_2$OCPh3); 1.63-1.54 (bm, 4H, Arom.C$^5$CH$_2$C$\underline{H}_2$— and —C$\underline{H}_2$CH$_2$OCPh$_3$); 1.40-1.23 (bm, 14H, —(C$\underline{H}_2$)$_7$—); 1.15 (s, 12H, 2×—C(C$\underline{H}_3$)$_2$CO$_2$0). C$_{48}$H$_{62}$O$_5$ requires: C=80.18%, H=8.69%; found: C=75.97%, H=8.37%. m/z (EI+): 718.0 (M$^+$, 2%); 641.5 ((M–Ph)$^+$, 60%).

Reference Example 8

Dimethyl 1,3-[5-(hydroxyundecyl)benzene]-bis(2,2-dimethylpropanoate)

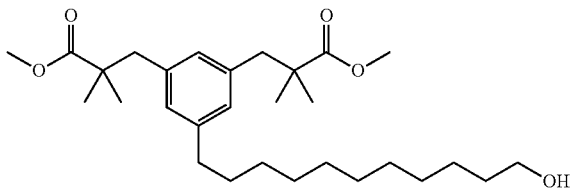 [SMILES: COC(=O)C(C)(C)Cc1cc(CCCCCCCCCCCO)cc(CC(C)(C)C(=O)OC)c1]

To dimethyl 1,3-[5-(triphenylmethoxyundecyl)benzene]-bis(2,2-dimethylpropanoate) (2.67 g, 3.71 mmol) dissolved in dichloromethane/methanol, 1:1 (20 ml) was added triisopropylsilane (2.0 ml, 1.55 g, 9.67 mmol) followed by four drops of concentrated hydrochloric acid. The reaction mixture was swirled thoroughly and stood at ambient temperature for 4 hr. Solvent was removed in vacuo to a white, viscous slurry and the crude product purified on silica (0 to 5% methanol/10% to 20% ethyl acetate/hexane) to yield the title compound (1.07 g, 2.24 mmol) as a clear, colourless, viscous oil.

$\delta^1$H (CDCl$_3$): 6.74 (s, 2H, Arom.C$^{4,6}$—$\underline{H}$); 6.65 (s, 1H, Arom.C$^2$—$\underline{H}$); 3.65 (s, 6H, 2×—CO$_2$C$\underline{H}_3$); 3.63 (t, 2H, —C$\underline{H}_2$OH); 2.78 (s, 4H, Arom.C$^{1,3}$C$\underline{H}_2$—); 2.50 (t, 2H, Arom.C$^5$C$\underline{H}_2$—); 1.58-1.51 (bm, 4H, Arom.C$^5$CH$_2$C$\underline{H}_2$— and —C$\underline{H}_2$CH$_2$OH); 1.36-1.26 (bm, 14H, —(C$\underline{H}_2$)$_7$—); 1.15 (s, 12H, 2×—C(C$\underline{H}_3$)$_2$CO$_2$—). C$_{29}$H$_{48}$O$_5$ requires: C=73.07%, H=10.15%; found: C=72.85%, H=10.18%. m/z (EI+): 476.4 (M$^+$, 5%).

Example 9

Dimethyl 3,3'-(5-(11-(((2-chlorophenoxy)(((3R,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)phosphoryl)oxy)undecyl)-1,3-phenylene)bis(2,2-dimethylpropanoate) (Compound 1)

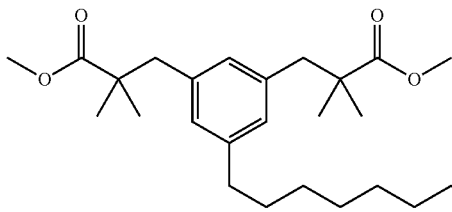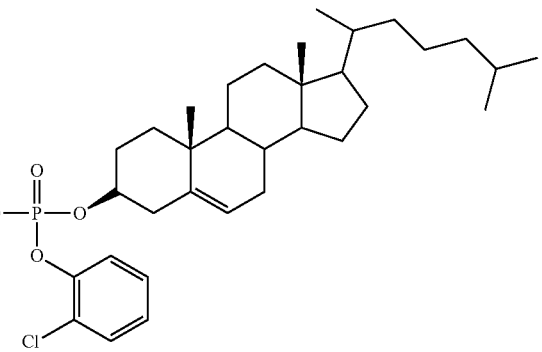

2-Chlorophenyl 3-O-cholesteryl phosphate, triethylammonium salt (1.45 g, 2.14 mmol) together with 1-(2-mesitylenesulphonyl)-3-nitro-1,2,4-triazole (1.25 g, 4.22 mmol) were dissolved in anhydrous pyridine (10 ml) and anhydrous 1-methylimidazole (2 ml) and the reaction mixture stirred at ambient temperature for 30 min. To this was then added dimethyl 1,3-[5-(hydroxyundecyl)benzene]-bis(2,2-dimethylpropanoate) (0.84 g, 1.76 mmol) dissolved in anhydrous pyridine (10 ml) and the reaction mixture stirred at ambient temperature overnight. Solvent was removed in vacuo to a slightly turbid, orange-yellow, viscous oil, and crude product was purified on silica (30% ethyl acetate/hexane) to yield the title compound (1.50 g, 1.45 mmol) as a clear, almost colourless, viscous oil.

$\delta^1$H (CDCl$_3$): 7.49 (d, 1H, ClPh.C$^3$$\underline{H}$); 7.40 (d, 1H, ClPh.C$^6$$\underline{H}$); 7.25 (t, 1H, ClPh.C$^4$$\underline{H}$); 7.12 (t, 1H, ClPh.C$^5$$\underline{H}$); 5.37 (bm, 1H, Chol.C$^6$$\underline{H}$); 4.37 (bm, 1H, —O$_3$PO-Chol.C$^3$ $\underline{H}$). 4.17 (m, 2H, —C$\underline{H}_2$OPO$_3$—); 3.66 (s, 6H, 2×—CO$_2$C$\underline{H}_3$); 2.79 (s, 4H, Arom. C$^{1,3}$C$\underline{H}_2$—); 2.51 (t, 2H, Arom.C$^5$C$\underline{H}_2$—); 2.41 and 1.99-1.10 (m and bm, 2H and 44H, Chol. C$^{alicyclic}$$\underline{H}$ and C$^{aliphatic}$$\underline{H}$ and —(C$\underline{H}_2$)$_9$—); 1.15 (s, 12H, 2×—C(C$\underline{H}_3$)$_2$CO$_2$—); 1.01 (s, 3H Chol.C$^{19}$$\underline{H}_3$); 0.91 (d, 3H, Chol.C$^{21}$$\underline{H}_3$); 0.87 (d, 6H, Chol.C$^{2425}$$\underline{H}_3$); 0.67 (s, 3H, Chol.$C^{18}\underline{H}_3$). $C_{62}H_{97}PO_8Cl$ requires: C=71.88%, H=9.34%; found: C=71.71%, H=9.36%. m/z (ES+): 1057.6 (MNa+, 20%).

Example 10

3,3'-(5-(11-(((((3R,10R,13R)-10,13-Dimethyl-17-(6-methylheptan-2-yl)-2,3,4,7,8,9,10,11,12,13,14,15,16,17-tetradecahydro-1H-cyclopenta[a]phenanthren-3-yl)oxy)(hydroxy)phosphoryl)oxy)undecyl)-1,3-phenylene)bis(2,2-dimethylpropanoic acid), ammonium salt (Compound 2)

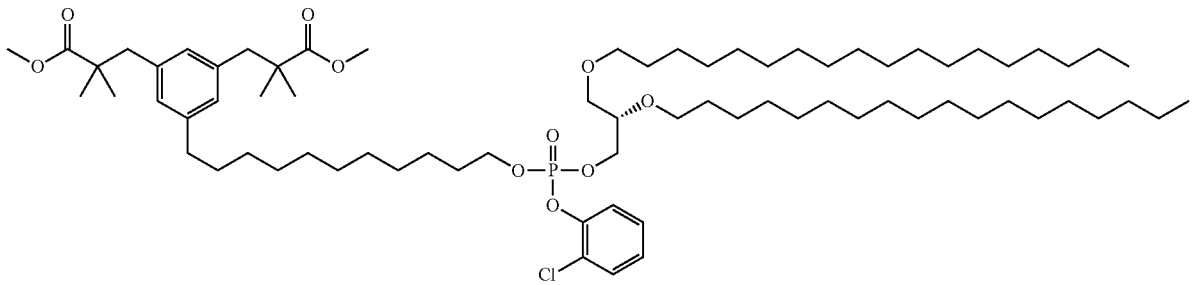 [SMILES: CCCCCCCCCCCCCCCCCCOC[C@@H](COP(=O)(OCCCCCCCCCCCc1cc(CC(C)(C)C(=O)OC)cc(CC(C)(C)C(=O)OC)c1)Oc1ccccc1Cl)OCCCCCCCCCCCCCCCCCC]

dimethyl 3,3'-(5-(11-(((2-chlorophenoxy)(((3R,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)phosphoryl)oxy)undecyl)-1,3-phenylene)bis(2,2-dimethylpropanoate) (1.50 g, 1.45 mmol) was dissolved in dioxane (10 ml) and to this was added lithium hydroxide solution (10% w/v, 10 ml) and the resultant two phase reaction mixture stirred vigorously to a homogeneous emulsion at 60° C. for 24 hr. The turbid single phase was poured into deionised water (200 ml) and acidified to ~pH=1.0 by dropwise addition of concentrated hydrochloric acid. The resultant dense, white precipitate was extracted into chloroform (2×200 ml) and the combined organic phases dried over anhydrous sodium sulphate. Solvent was removed in vacuo to a clear, almost colourless gum. Crude product was purified on $C_{18}$ reverse-phase silica (dichloromethane/methanol/water/conc. ammonium hydroxide, 2:6:1:0.5) to give a colourless, amorphous solid which was triturated with diethyl ether to yield the title compound (1.06 g, 1.12 mmol) as a white, powdery solid.

$\delta^1H$ ($CHCl_3$): 6.83 (s, 2H, $Arom.C^{4-6}\underline{H}$); 6.79 (s, 1H, $Arom.C^2\underline{H}$); 5.36 (m, 1H $Chol.C^6\underline{H}$); 3.95 (bm, 1H, —$O_3POChol.C^3\underline{H}$); 3.83 (dd, 2H, —$C\underline{H}_2OPO_3$—); 2.80 (s, 4H, $Arom.C^{1,3}C\underline{H}_2$—); 2.53 (t, 2H, $Arom.C^5C\underline{H}_2$—); 2.50-2.31 and 2.05-1.50 (2×bm, 2H and 6H, $Chol.C^{1,2,4,7}\underline{H}_2$—); 1.48-1.08 (bm, 38H, $Chol.C^{alicyclic}$—$\underline{H}$ and $C^{aliphatic}$—$\underline{H}$ and —$(C\underline{H}_2)_9$—); 1.13 (s, 12H, 2×—$C(C\underline{H}_3)_2CO_2$—); 1.02 (s, 3H, $Chol.C^{19}\underline{H}_3$); 0.93 (d, 3H, $Chol.C^{21}\underline{H}_3$); 0.87 (d, 6H, $Chol.C^{24-25}\underline{H}_3$); 0.70 (s, 3H, $Chol.C^{18}\underline{H}_3$). $C_{60}H_{93}PO_8Cl.3(C_6H_{15}N)$ requires: C=68.39%, H=10.42%, N=4.43%: found: C=69.07%, H=10.30%, N=2.36%. m/z (ES−): 895.6 (M−H, 100%), 527.5 (M−Chol, 10%); 465.6 (Chol.$OPO_3H)^−$, 20%).

Example 11

Dimethyl 3,3'-(5-(11-((((S)-2,3-bis(octadecyloxy)propoxy)(2-chlorophenoxy)phosphoryl)oxy)undecyl)-1,3-phenylene)bis(2,2-dimethylpropanoate) (Compound 3)

To 2-chlorophenyl (R)-2,3-di(octadecyloxy)propyl phosphate, triethylammonium salt (0.522 g, 0.59 mmol) dissolved in a mixture of anhydrous pyridine (20 ml) and 1-methylimidazole (2 ml), was added 1-(2-mesitylenesulphonyl)-3-nitro-1,2,4-triazole (0.25 g, 0.84 mmol) and the resultant turbid reaction mixture stirred at ambient temperature for 30 min. To this was then added dimethyl 1,3-(5-hydroxyundecyl)benzene-bis(2,2-dimethylpropanoate) (0.248 g, 0.52 mmol) and the reaction mixture was stirred at ambient temperature overnight. Further 1-(2-mesitylenesulphonyl)-3-nitro-1,2,4-triazole (0.25 g, 0.84 mmol) was then added and the reaction mixture stirred at ambient temperature for a further four hours. Solvent was then removed in vacuo and the resultant turbid oily liquid was resuspended in ethyl acetate (100 ml) and washed with deionised water (2×100 ml). The organic phase was dried over anhydrous magnesium sulphate and solvent removed in vacuo to a clear, golden brown oil. The crude product was purified on silica (20% ethyl acetate/hexane) to yield the title compound (0.258 g, 0.21 mmol) as a white, waxy solid.

$\delta^1$H (CDCl$_3$): 7.47 (d, 1H, ClPh.C$^3$—$\underline{H}$); 7.39 (d, 1H, ClPh.C$^6$—$\underline{H}$); 7.22 (t, 1H, ClPh.C$^4$—$\underline{H}$; 7.12 (t, 1H, ClPh.C$^5$—$\underline{H}$); 6.74 (s, 2H, Arom.C$^{4-6}$—$\underline{H}$); 6.65 (s, 1H, Arom.C$^2$—$\underline{H}$); 4.32-4.15 (bm, 4H, 2×—O$_3$POC$\underline{H}_2$—); 3.65 (s, 6H, 2×—CO$_2$CH$\underline{H}_3$); 3.57-3.38 (bm, 7H, —OC$\underline{H}$< and 3×—OC$\underline{H}_2$—); 2.78 (s, 4H, Arom.C$^{1-2}$—C$\underline{H}_2$—); 2.50 (t, 2H, Arom.C$^5$—C$\underline{H}_2$—); 1.69 (m, 2H, —O$_3$POCH$_2$C$\underline{H}_2$—); 1.57 (m, 6H, 3×—OC$\underline{H}_2$—); 1.25 (bm, 76H, —(C$\underline{H}_2$)$_8$— and 2×—(C$\underline{H}_2$)$_{15}$—); 1.15 (s, 12H, 2×—C(C$\underline{H}_3$)$_2$CO$_2$—); 0.88 (t, 6H, 2×—O(CH$_2$)$_{17}$C$\underline{H}_3$). m/z (ES, +90V); 1267.7 (MNa$^+$, 100%); 1245.8 (MH+, 35%. Mp.=27.0-27.5° C. (uncorrected).

Example 12

3,3'-(5-(11-((((S)-2,3-Bis(octadecyloxy)propoxy)(hydroxy)phosphoryl)oxy)undecyl)-1,3-phenylene)bis(2,2-dimethylpropanoic acid), ammonium salt (Compound 4)

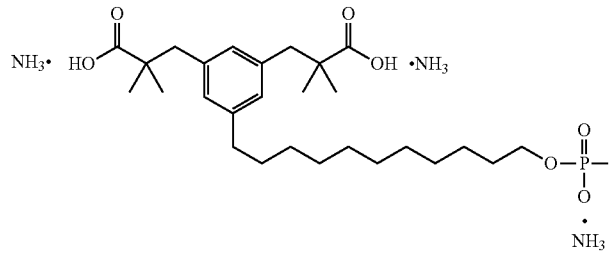

dimethyl 3,3'-(5-(11-((((S)-2,3-bis(octadecyloxy)propoxy)(2-chlorophenoxy)phosphoryl)oxy)undecyl)-1,3-phenylene)bis(2,2-dimethylpropanoate) (0.255 g, 0.20 mmol) was dissolved in dioxane (2 ml) and to this was added 10% aqueous lithium hydroxide solution (1 ml). The two phase reaction mixture was stirred vigorously at 60° C. overnight. The single phase reaction mixture was poured into deionised water (50 ml) and acidified to pH~1.0 with concentrated hydrochloric acid. The resultant dense white precipitate was extracted into chloroform (3×50 ml) and the combined organic phases evaporated in vacuo to an amorphous white solid. Crude product was purified by reverse-phase silica (Merck RP-18, dichloromethane/methanol/water, 4:12:3, +2% conc. ammonia) to yield the title compound (0.101 g, 0.09 mmol) as a fine, white powdery solid.

$\delta^1$H (CDCl$_3$); 6.98 (s, 1H, Arom.C$^2$$\underline{H}$); 6.74 (s, 2H Arom.C$^{4-6}$—$\underline{H}$); 3.90-3.81 (bm, 4H, 2×—O$_3$POC$\underline{H}_2$—); 3.60-3.40 (bm, 7H, —OC$\underline{H}$< and 3×—OC$\underline{H}_2$—); 2.76 (s, 4H, Arom.C$^{1-3}$—C$\underline{H}_2$—); 2.56 (t, 2H, Arom.C$^5$—C$\underline{H}_2$—); 1.60-1.55 (bm, 6H, —O$_3$POCH$_2$C$\underline{H}_2$— and 2×—OCH$_2$C$\underline{H}_2$—); 1.25 (bm, 76H, —(C$\underline{H}_2$)$_8$— and 2×—(C$\underline{H}_2$)$_{15}$—); 1.16 (s, 12H, —C(C$\underline{H}_3$)$_2$CO$_2$—); 0.88 (t, 6H, 2×—O(CH$_2$)$_{17}$C$\underline{H}_3$). m/z (ES, +27V): 1124.7 (MNH$_4^+$, 35%), 1107.8 (MH$^+$, 100%).

Reference Example 13

Methyl 16-hydroxyhexadecanoate

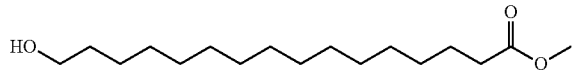 [SMILES: COC(=O)CCCCCCCCCCCCCCCO]

16-Hydroxyhexadecanoic acid (10.28 g, 37.73 mmol) was suspended in methanol (80 ml) and to this was added one drop of concentrated sulphuric acid and the reaction mixture refluxed at 80° C. for 2 hr. The cooled reaction mixture was then poured into saturated sodium bicarbonate solution (250 ml) and extracted into ether (2×250 ml). The combined organic phases were dried over anhydrous magnesium sulphate and the solvent removed in vacuo to yield the title compound (7.78 g, 27.16 mmol) as a lustrous white crystalline solid.

$\delta^1$H (CDCl$_3$); 3.66 (s, 2H, CO$_2$C$\underline{H}_3$), 3.63 (t, 2H, C$\underline{H}_2$OH); 2.29 (t, 2H, —C$\underline{H}_2$CO$_2$—); 1.63-1.53 (bm, 4H, —C$\underline{H}_2$CH$_2$OH and —C$\underline{H}_2$CH$_2$CO$_2$—); 1.36-1.24 (bm, 2H, —(C$\underline{H}_2$)$_{11}$—). C$_{17}$H$_{34}$O$_3$ requires: C=71.28%, H=11.96%; found: C=71.35%, H=12.07%. m/z (ES, 27V); 287.1 (MH$^+$, 100%).

Reference Example 14

Methyl 16-(triphenylmethoxy)hexadecanoate

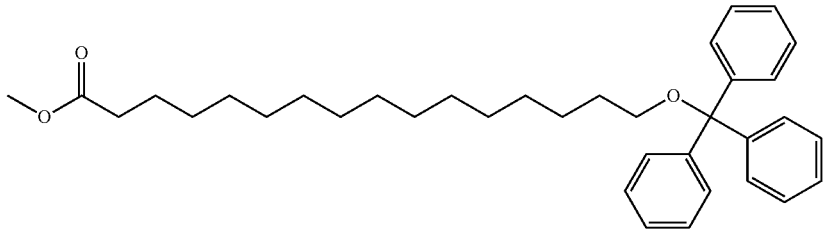 [SMILES: COC(=O)CCCCCCCCCCCCCCCOC(c1ccccc1)(c1ccccc1)c1ccccc1]

To methyl 16-hydroxyhexadecanoate (6.0 g, 21.0 mmol) dissolved in anhydrous dichloromethane (150 ml) was added anhydrous triethylamine (3.6 ml, 2.61 g, 25.8 mmol) followed by triphenylmethyl chloride (6.42 g, 23.0 mmol) and the reaction mixture stirred at ambient temperature overnight. Solvent was removed in vacuo to yield a cream coloured crystalline solid. The crude product was purified on silica (5% ether/hexane) to yield the title compound (9.32 g, 17.6 mmol) as a white crystalline solid.

$\delta^1$H (CDCl$_3$); 7.46-7.42 and 7.31-7.19 (2×bm, 5H and 10H, C$^{trityl}$—H); 3.66 (s, 3H—CO$_2$CH$_3$); 3.04 (t, 2H, —CH$_2$OCPh$_3$); 2.30 (t, 2H, —CH$_2$CO$_2$—); 1.64-1.57 (bm, 4H, —CH$_2$CH$_2$OCPh$_3$ and —CH$_2$CH$_2$CO$_2$—); 1.28-1.24 (bm, 22H, —(CH$_2$)$_{11}$—), C$_{25}$H$_{48}$O$_3$ requires: C=81.77%, H=9.15%; found: C=81.85%, H=9.18%. m/z (ES+): 551.3 (MNa$^+$, 20%); 243.1 (CPh$_3$, 100%). Mp.=52.54° C. (uncorrected).

Reference Example 15

16-Triphenylmethoxy-1-hexadecanol

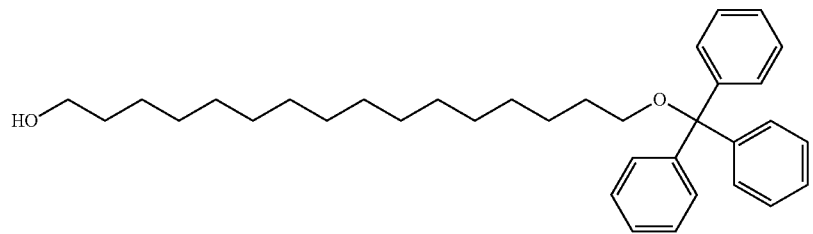 [SMILES: OCCCCCCCCCCCCCCCCOC(c1ccccc1)(c1ccccc1)c1ccccc1]

To a suspension of lithium aluminium hydride (0.73 g, 19.2 mol) in anhydrous tetrahydrofuran, stirred vigorously at −0° C. in an ice bath, was added dropwise a solution of methyl 16-(triphenylmethoxy)hexadecanoate (9.0 g, 17.0 mmol). The reaction mixture was allowed to attain ambient temperature while stirring overnight. To the vigorously stirring reaction mixture was then added dropwise, deionised water (0.73 ml), followed by sodium hydroxide solution (3M, 0.73 ml), and finally deionised water (2.19 ml). The pale grey precipitate was removed by filtration and the resultant clear colourless supernatant was evaporated in vacuo to yield the title compound (7.97 g, 15.9 mmol) as a clear, colourless viscous oil which slowly solidified to a white crystalline solid.

$\delta^1$H (CDCl$_3$); 7.46-7.42 and 7.32-7.19 (2×bm, 5H and 10H, C$^{trityl}$—H); 3.63 (t, 2H, —CH$_2$OH); 3.04 (t, 2H, —CH$_2$OCPh$_3$); 1.64-1.54 (bm, 4H, —CH$_2$CH$_2$OH and —CH$_2$OCPh$_3$); 1.43-1.24 (bmin, 24H, —(CH$_2$)$_{12}$—), C$_{35}$H$_{48}$O$_2$ requires: C=83.95%, H=9.66%; found C=84.14%, H=9.72%. m/z (EI+): 500.5 (M$^+$, 0.03%); 423.6 (M$^+$-Ph, 1%); 243.3 (CPh$_3{}^+$, 45%).

Reference Example 16

16-Bromo-1-(triphenylmethoxy)hexadecane

To a stirred solution of 16-triphenylmethoxy-1-hexadecanol (7.95 g, 15.9 mmol) dissolved in anhydrous dichloromethane (250 ml) was added anhydrous triethylamine (4.40 ml, 3.19 g, 31.6 mmol) followed by tetrabomomethane (5.79 g, 17.5 mmol) then portionwise, triphenylphosphine (4.58 g, 17.5 mmol). The darkening reaction mixture was stirred at ambient temperature for 2 hr then solvent removed in vacuo to give a dark red-brown viscous oil. The crude product was purified on silica (0 to 5% ether/hexane) to yield the title compound (6.93 g, 12.3 mmol) as a white crystalline solid.

$\delta^1$H (CDCl$_3$); 7.47-7.43 and 7.32-7.19 (2×bm, 6H and 9H, C$^{trityl}$—H; (3.41 (t, 2H, —CH$_2$Br); 3.05 (t, 2H, —CH$_2$OCPh$_3$); 1.90-1.81 (bm, 2H, —CH$_2$CH$_2$Br); 1.64-1.57 (bm, 2H, —CH$_2$OCPh$_3$); 1.45-1.25 (bm, 24H, —(CH$_2$)$_{12}$—). C$_{35}$H$_{47}$OBr requires: C=74.58%, H=8.41%, found C=74.72%, H=8.45%. m/z (EI+): 563/565 (M$^+$, 1%); 485/487 (M$^+$-Ph, 2%); 243 (CPh$_3{}^+$, 100%). mp.=59-60° C. (uncorrected).

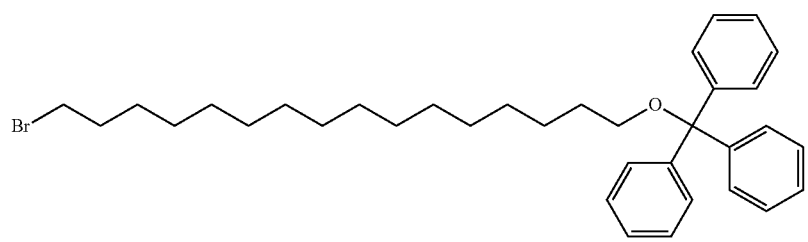 [SMILES: BrCCCCCCCCCCCCCCCCOC(c1ccccc1)(c1ccccc1)c1ccccc1]

Reference Example 17

17-Triphenylmethoxy-1-heptadecene

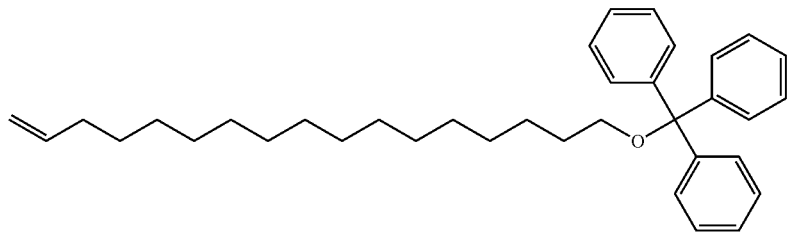 [SMILES: C=CCCCCCCCCCCCCCCCOC(c1ccccc1)(c1ccccc1)c1ccccc1]

16-Bromo-1-(triphenylmethoxy)hexadecane (5.04 g, 8.94 mmol) and triphenylphosphine (2.46 g, 9.38 mmol) were together suspended in anhydrous acetonitrile (5 ml) and stirred under an argon atmosphere at 80° C. for 36 hr. The resultant clear, pale yellow gum was allowed to cool then dissolved in anhydrous tetrahydrofuran (50 ml) and stirred at ~0° C. in an ice bath while a solution of lithium diisopropylamide in heptane/ethylbenzene/tetrahydrofuran (2M, 9.0 ml, 18.0 mmol) was added dropwise. After stirring for a further 10 min, paragormaldehyde (0.535 g, 17.98 mmol eqiv. $CH_2O$) was added and the reaction mixture stirred at ~0° C. for 1 hr then allowed to attain ambient temperature while stirring overnight. The reaction mixture was poured into saturated ammonium chloride solution (100 ml) and extracted into diethyl ether (100 ml). The organic phase was washed with brine (100 ml) then dried over anhydrous sodium sulphate. Solvent was removed in vacuo to give a clear, golden brown viscous oil. The crude product was purified on silica (hexane) to yield the title compound (1.28 g, 2.58 mmol) as a white, waxy crystalline solid.

$\delta^1H$ ($CDCl_3$); 7.47-7.43 and 7.32-7.20 (2×bm, 6H and 9H, $C^{trityl}$—H); 5.89-5.75 (cm, 1H, —C$\underline{H}$=$CH_2$); 5.03-4.90 (bm, 2H, —CH=C$\underline{H}_2$); 3.05 (t, 2H, —C$\underline{H}_2$); 3.05 (t, 2H, —C$\underline{H}_2$OC$Ph_3$); 2.03 (m, 2H, —C$\underline{H}_2$CH=$CH_2$); 1.66-1.57 (bm, 2H, —C$\underline{H}_2$$CH_2$OC$Ph_3$); 1.37-1.19 (bm, 24H, —(CH2)12-). $C_{36}H_{48}O$ requires: C=87.04%, H-9.74%1 found: C=87.31%, H=9.76%. m/z (EI+): 496.5 (M+, 1%): 419.6 (M+Ph, 0.5%); 243.3 ($CPh_3$+90%).

Reference Example 18

Dimethyl 1,3-[5-(triphenylmethoxyheptadecyl)benzene]-bis(2,2-dimethylpropanoate)

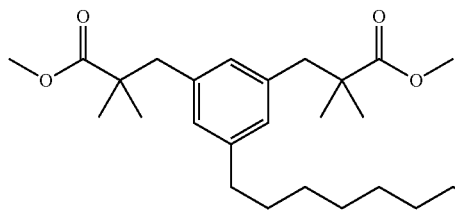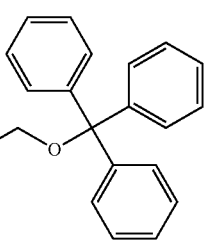

To a solution of 17-triphenylmethoxy-1-heptadecene (1.38 g, 2.78 mmol) in anhydrous tetrahydrofuran (20 mo) stirred at ~0° C. in an ice bath, was added dropwise a solution of 9-borabicyclo [3.3.1]nonane in tetrahydrofuran (0.50M, 6.70 ml, 3.35 mmol) and the reaction mixture stirred at ~0° C. for 3 hr. To this was then added dimethyl 1,3-(5-bromobenzene)-bis(2,2-dimethylpropanoate) (0.974 g, 2.53 mmol) together with tetrakis(triphenylphosphine) palladium(o) (0.20 g, 0.17 mmol), anhydrous potassium carbonate (0.85 g) and anhydrous dimethyformamide (7.5 ml) and the reaction mixture refluxed at 85° C. under an argon atmosphere overnight. The reaction mixture was cooled to ambient temperature and poured into saturated ammonium chloride solution (100 ml) and extracted into ethyl acetate (100 ml). The organic phase was washed with further saturated ammonium chloride solution (2×100 ml), dried over anhydrous sodium sulphate and solvent removed in vacuo. Crude product was purified on silica (20% diethyl ether/hexane) to yield the title compound (1.14 g, 1.42 mmol) as a soft waxy white solid.

$\delta 1H$ ($CDCl_3$): 7.46-7.42 and 7.31-7.19 (2×bm, 5H and 10H, $C^{trityl}$—H); 6.75 (s, 2H, Arom, C4.6-H); 6.67 (s, 1H, Arom.C2-H); 3.65 (s, 6H, x —CO2CH3); 3.04 (T, 2H, —CH2OCPh3); 2.78 (s, 4H, Arom, C1,3-CH2); 2.51 (t, 2H, Arom.C5-CH2); 1.64-1.54 (bm, 6H, Arom.C5CH2CH2- and CH2CH2CH2OCPh3); 1.26-1.24 (bm, 24H (CH2)12); 1.15 (S, 12 h-C(CH3)2CO2-); $C_{53}H_{74}O_5$ requires: c=80.75%, H=9.29%, found: C=77.44%, H=8.93%, m/z (EI+): 802.5 (M+, 0.001%); 243.4 ($CPh_{3+, 50}$%).

Reference Example 19

Dimethyl 1,3-[5-hydroxyheptadecyl)benzene]-bis(2,2-diemethylpropanoate

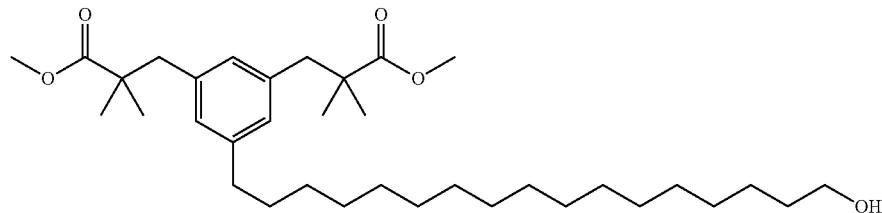 [SMILES: COC(=O)C(C)(C)Cc1cc(CCCCCCCCCCCCCCCCCO)cc(CC(C)(C)C(=O)OC)c1]

To dimethyl 1,3-[5-triphenylmethoxyheptadecyl)benzene]-bis(2,2-diemethylpropanoate) (1.14, 1.42 mmol) dissolved in dichloromethane/methanol, 1:1 (10 ml), was added triisopropylsilane (1.00 ml, 0.773 g, 4.88 mmol) followed by two drops of concentrated hydrochloric acid. The reaction mixture was swirled thoroughly then stood at ambient temperature for 3 hr. Solvent was removed in vacuo, and the crude product purified on silica (10% to 20% ethyl acetate/hexane) to yield the title compound (0.53 g, 0.94 mmol) as a clear, colourless viscous oil which solidified to a white, crystalline solid on protracted standing.

δ1H (CDCl3): 6.74 (s, 2H. Arom.C4,6-H); 6.64 (s, 1H, Arom.C2-H); 3.65 (s, 6H, 2×—CO2CH3); 3.63 (t, 2H, —CH2OH); 2.78 (s, 4H, Arom.C1,3-CH$_2$); 2.51 (t, 2H—CH2OH); 1.61-1.52 (gm, 2H, —CH2CH2OH); 1.36-1.23 (bm, 28H, —(CH2)14-); 1.14 (s, 12H, 2×—C(CH3) 2CO2-). $C_{35}H_{60}O_5$ requires: C=74.95%, H=10.78%; found: C=74.88%, H=10.80%. m/z (EI): 560.6 (M+2%). mp=25.26° C. (uncorrected).

Example 20

Dimethyl 3,3'-(5-(17-(((2-chlorophenoxy)(((3R,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)phosphoryl)oxy)heptadecyl)-1,3-phenylene)bis(2,2-dimethylpropanoate) (Compound 5)

2-Chlorophenyl 3-O-cholesteryl phosphate, triethylammonium salt (0.58 g, 0.86 mmol) together with 1-(2-mesitylenesulphonyl)-3-nitro-1,2,4-triazole (0.85 g, 2.86 mmol) were dissolved in anhydrous pyridine (4 ml) and anhydrous 1-methylimidazole (0.8 ml), and the reaction mixture stirred at ambient temperature for 30 min. To this was then added dimethyl 1,3-[5-hydroxyheptadecyl)benzene]-bis(2,2-dimethylpropanoate) (0.39 g, 0.70 mmol) dissolved in anhydrous pyridine (4 ml) and the reaction mixture stirred at ambient temperature overnight. Solvent was removed in vacuo to a yellow, viscous oil and crystalline solid, and crude product was purified on silica (20% ethyl acetate/hexane) to yield the title compound (0.40 g, 0.36 mmol) as a clear, colourless, viscous oil.

δ1H (CDCl$_3$): 7.47 (d, ClPh C$^3$—H); 7.40 (d, 1H, ClPh C$^6$—H); 7.23 (t, 1H, ClPh C$^4$—H); 7.09 (t, 1H, ClPh C$^5$—H); 6.74 (s, 2H, Arom.C$^{4-6}$—H); 6.65 (s, 1H, Arom.C$^2$—H); 5.36 (bm, 1H, Chol. C$^6$—H); 4.33 (bm, 1H, —O$_3$PO-Chol.C$^3$—H); 4.17 (dd, 2H, —CH$_2$OPO$_3$—); 3.65 (s, 6H, 2×—CO$_2$CH$_3$); 2.78 (s, 4H, Arom.C$^{1,3}$CH$_2$—); 2.50 (t, 2H, Arom.C$^5$CH$_2$—); 2.47 and 2.03-1.00 (m and bm, 2H and 56H, Chol.C$^{alicyclic}$—H and C$^{aliphatic}$—H and —(CH$_2$)$_{15}$—); 1.14 (s, 12H, 2×—CCH$_3$)$_2$CO$_2$—); 1.01 (s, 3H, Chol.C$^{19}$H$_3$); 0.91 (d, 3H, Chol.C$^{21}$H$_3$); 0.86 (d, 6H, Chol.C$^{24,25}$H$_3$); 0.67 (s, 3H, Chol.C$^{18}$H$_3$); $C_{68}H_{108}PO_8Cl$ requires: C=72.92%, H=9.72%; found: C=72.96%, H=9.72%. m/z (ES+): 1136.4 (MNH$_4^+$, 40%).

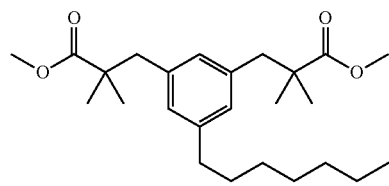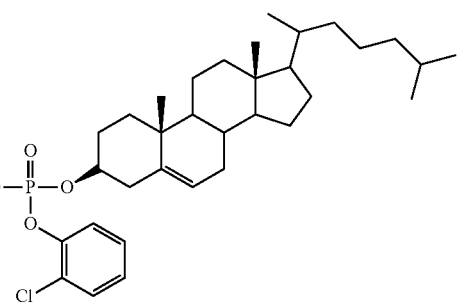

Example 21

3,3'-(5-(17-(((((3R,10R,13R)-10,13-Dimethyl-17-(6-methylheptan-2-yl)-2,3,4,7,8,9,10,11,12,13,14,15,16,17-tetradecahydro-1H-cyclopenta[a]phenanthren-3-yl)oxy)(hydroxy)phosphoryl)oxy)heptadecyl)-1,3-phenylene)bis(2,2-dimethylpropanoic acid), Ammonium Salt

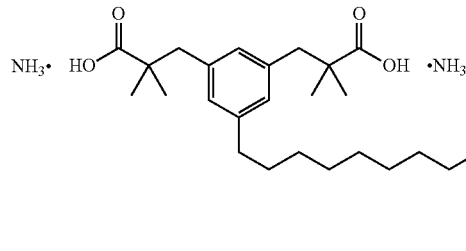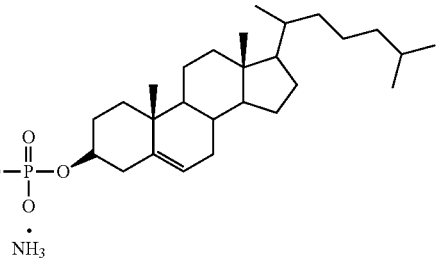

To dimethyl 3,3'-(5-(17-(((2-chlorophenoxy)(((3R,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)phosphoryl)oxy)heptadecyl)-1,3-phenylene)bis(2,2-dimethylpropanoate) (0.41 g, 0.36 mmol) dissolved in dioxane (2.5 ml) was added lithium hydroxide solution (10% w/v, 2.5 ml) and the resultant two phase reaction mixture was stirred vigorously to a homogenous emulsion at 60° C. overnight. The turbid, viscous emulsion was then dissolved in deionised water (50 ml) and acidified to pH=1.0 by dropwise addition of concentrated hydrocloric acid. The resultant dense, white precipitate was extracted into chloroform (2×100 ml) and the combined organic phases dried over anhydrous sodium sulphate, and solvent removed in vacuo to give a fine white crystalline solid. Crude product was purified on $C_{18}$ reverse phase silica (dichloromethane/methanol/water, 2:6:1; 1% concentrated ammonium hydroxide) to yield the title compound (0.18 g, 0.14 mmol) as a fine white solid.

δ1H (CD$_3$OD): 6.71 (s, 1H, Arom.C$^2$—$\underline{H}$); 6.67 (s, 1H, Arom.C$^{4,6}$—$\underline{H}$); 5.23 (m, 1H, Chol.C$^6$—$\underline{H}$); 3.83 (bm, 1H, —O$_3$PO-Chol.C$^3$—$\underline{H}$); 3.74 (bm, 2H, —C$\underline{H}_2$OPO$_3$—); 2.67 (s, 4H, Arom.C$^{1,3}$C$\underline{H}_2$—); 2.43 (t, 2H, Arom.C$^5$C$\underline{H}_2$—); 2.38-2.22 and 1.87-1.70 (2×bm, 2H and 6$^{tH}$, Chol.C$^{1,2,4,7}$$\underline{H}_2$—); 1.47-1.05 (bm, 50H, Chol.C$^{alicyclic}\underline{H}$ and C$^{aliphatic}\underline{H}$ and —(C$\underline{H}_2$)$_{15}$—); 1.03 (s, 12H, 2×—C(C$\underline{H}_3$)$_2$CO$_2$—); 0.89 (s, 3H, Chol.C$^{19}\underline{H}_3$); 0.77 (d, 3H, ChoIC$^{21}\underline{H}_3$); 0.74 (d, 3H, Chol.C$^{26,27}\underline{H}_3$); 0.56 (s, 3H, Chol.C$^{18}\underline{H}_3$). m/z (ES-); 980.0 (M$^-$, 100%).

Example 22

Transfection of Chinese Hamster Ovary (CHO) Cells Using Lipopolyplexes

Materials

Plasmid pEGlacZ containing the bacterial β-galactosidase gene under the control of the human cytomegalovirus immediate early promoter was constructed using standard molecular cloning techniques. The 7676 base pair (bp) plasmid was derived by cleavage of pGFP-N1 (Clontech) with HindIII and BclI to remove the reporter gene fragment. The β-galactosidase coding region from pSV-β-galactosidase (Promega) was then inserted via a HindIII to BamHI fragment. Plasmid DNA was then purified using an anion-exchange column (Qiagen Ltd). The average molecular weight per base pair was calculated to be 620.84 Da (310.5 Da for a monophosphorylated nucleotide). The amount of negative charge on the plasmid was then determined on the basis that a single negative charge is associated with each nucleotide.

R26 peptide, a human protamine P2 protein-derived peptide, comprising the amino acid sequence: YHRRQRSR-RRRRRSGRHRRRHRRGCR, was supplied by Peptide Protein Research Ltd., Bishop's Waltham, U.K., and were synthesized by Fmoc solid phase peptide chemistry according to the method of Atherton and Sheppard. (Ref: Atherton, E.; Sheppard, R. C. (1989). Solid Phase peptide synthesis: a practical approach. Oxford, England: IRL Press).

Dioleoylphosphatidylcholine (DOPC), oleic acid (cis-octadecanoic acid), cholesterol, cholesterol hemisuccinate (CHEMS), dry chloroform and buffer components were supplied by Sigma-Aldrich Company Ltd. Dorset, UK. Radiolabelled 3H-cholesterol (1-alpha, 2-alpha (n)-3H cholesterol) was supplied by Amersham, UK Methods Liposome Preparation Compound 2 (Example 10), DOPC, cholesterol and oleic acid to a total of 60 µmol per batch in various combinations as shown in Table 1 together with 2 µl 3H cholesterol, were dissolved in 4 mL dry chloroform in a 100 ml round bottom flask. Lipid films were formed by rotary evaporation at 60° C. and further dried on a freeze drier overnight. Rehydration of the lipid film was performed by adding 4 mL of deionised water and 30 mL 1M NaOH at 60° C. with vigorous agitation in the presence of 1.5-2 mM diameter glass beads, taking care to maintain pH in the range 7.5 to 8.0, resulting in the formation of multi-lamellar vesicles (MLVs).

Small uni-lamellar vesicles (SUVs) were produced from the MLVs using a French Press (SLM Aminco) at a pressure of 1000 psi. After preparation, 20 mL aliquots were removed for scintillation counting to determine the final lipid concentration. Particle size of the SUV preparations was checked by dynamic light Scattering Equipment (Coulter N4 Plus) and found to in the unimodal diameter range of 80 to 110 nm.

TABLE 1

| Lipid | Batch 1 mol % | Batch 2 mol % | Batch 3 mol % | Batch 4 mol % |
|---|---|---|---|---|
| Compound 2 | 1 | 5 | 20 | 40 |
| DOPC | 40 | 40 | 40 | 60 |
| Cholesterol | 39 | 35 | 20 | 0 |
| Oleic acid | 20 | 20 | 20 | 0 |

Polyplex Preparation

Stock solutions of R26 peptide as a DNA condensing agent at 144 µg/ml and plasmid DNA at 60 µg/ml were prepared in de-ionized water. Equal volumes of each were mixed by adding the plasmid DNA drop-wise to the R26 solution with vortexing. The charge ratio of the polyplex was 3.9:1 (peptide positive charged residues to DNA negative charged phosphates).

Lipopolyplex Preparation

The polyplex preparation was diluted in 10 mM HEPES buffer pH 8 to 15 µg/ml DNA equivalent. The liposome batches 1 to 4 were diluted in the same buffer to four concentrations such that final lipid:DNA phosphate ratios were 2:1, 5:1, 12:1 and 36:1. Lipopolyplexes were formed by adding equal volumes of polyplex solution drop-wise to liposome suspension with vortexing.

CHO Cell Transfection

CHO cells were seeded into 24-wellplates at 100 000 cells per well in Opti-MEM (Gibco BRL) media containing 10% dialysed foetal calf serum (FCS, Gibco BRL) and maintained 37° C. in 5% $CO_2$ incubator for 24 h before the experiment. The adherent cells were washed once in Opti-MEM (Gibco BRL) prior to transfection. Washed medium was removed and replaced with 0.5 ml of Opti-MEM to which 167 µl of lipopolyplex was added (5 µg DNA equivalent). Individual lipopolyplex preparations were tested in triplicate wells. Cells were incubated for a further 4 h at 37° C. in 5% $CO_2$ before removal of the medium and non-cell associated lipopolyplex and addition of 1 ml of fresh medium (Dulbecco's modified Eagle's medium (DMEM), plus glutamate, asparagine, adenosine, guanosine, cytidine, uridine, thymidine and 10% FCS.

Cells were cultured for a further 72 h before harvesting, the medium was aspirated and the cells washed twice with 1 ml phosphate buffered saline. Cells were lysed by the addition of 200 µl per well of lysis buffer (Promega) and the plate was agitated on an orbital mixer for 15 min. The lysates were transferred to individual Eppendorf tubes, taking care to remove attached cells by scraping with a pipette tip prior to removal. Cell debris was removed by centrifugation in a microfuge for 5 min followed by transfer of the supernatant into clean Eppendorf tubes.

Levels of β-galactosidase (β-gal) activity were determined using a colorimetric enzyme assay kit (Promega) as follows: 50 µl of cell extract was incubated with the kit substrate, O-nitrophenyl-β-D-galactopyranoside in buffer solution for 30 min at 37° C. The reaction was stopped by the addition of 150 µl of 1M sodium carbonate and the absorbance measured at 420 nm (Multiskan Ascent plate reader, Labsystems). Absorbance values were interpolated from a calibration curve to give enzyme activity in mU per ml. In turn these values were normalised in reference to lysate protein concentration as determined by a BCA assay kit (Pierce) and expressed as mU of β-gal per mg of protein.

Results

Results are show in FIG. 1. Lipopolyplexes containing cholesterol, oleic acid and DOPC mixtures resulted in little or no expression of β-galactosidase in the absence of Compound 2 or at 1 mol % Compound 2, whereas for preparations at the lower lipid to DNA ratio of 2:1 (Batch 4), reporter gene expression increased with increasing content of Compound 2.

Expression was highest when the cholesterol/oleic acid components had been totally substituted with Compound 2 at 40 mol %. At higher lipid to DNA ratios expression levels were not significant except for the preparation at 5:1 lipid to DNA and 20 mol % Compound 2.

Example 23

Materials

Materials were as described in Example 22.

Methods

Liposome Preparation

An anionic liposome composition was evaluated comprising DOPC and CHEMS in the presence and absence of Compound 2. The protocol in Example 22 was followed to prepare SUVs using combinations of the former components in molar ratios as shown in Table 2. The unimodal diameters of these SUVs were 125 nm and 143 nm for Batches 5 and 6 respectively.

TABLE 2

| Lipid | Batch 5 mol % | Batch 6 mol % |
|---|---|---|
| Compound 2 | 20 | 0 |
| DOPC | 60 | 60 |
| CHEMS | 20 | 40 |

Polyplex Preparation

Stock solutions of R26 peptide as a DNA condensing agent at 144 µg/ml and plasmid DNA at 60 µg/ml were prepared in de-ionized water. Equal volumes of each were mixed by adding the plasmid DNA drop-wise to the R26 solution with vortexing. The charge ratio of the polyplex was 3.9:1 (peptide positive charged residues to DNA negative charged phosphates).

Lipopolyplex Preparation

The protocol described in Example 22 was followed. For liposome batches 5 & 6, dilutions were made to the ratios 0.6:1, 0.8:1 and 5.5:1. Lipopolyplexes were formed by adding equal volumes of polyplex solution drop-wise to liposome suspension with vortexing.

CHO Cell Transfection

The protocol of Example 22 was followed.

Results

Figure 2:
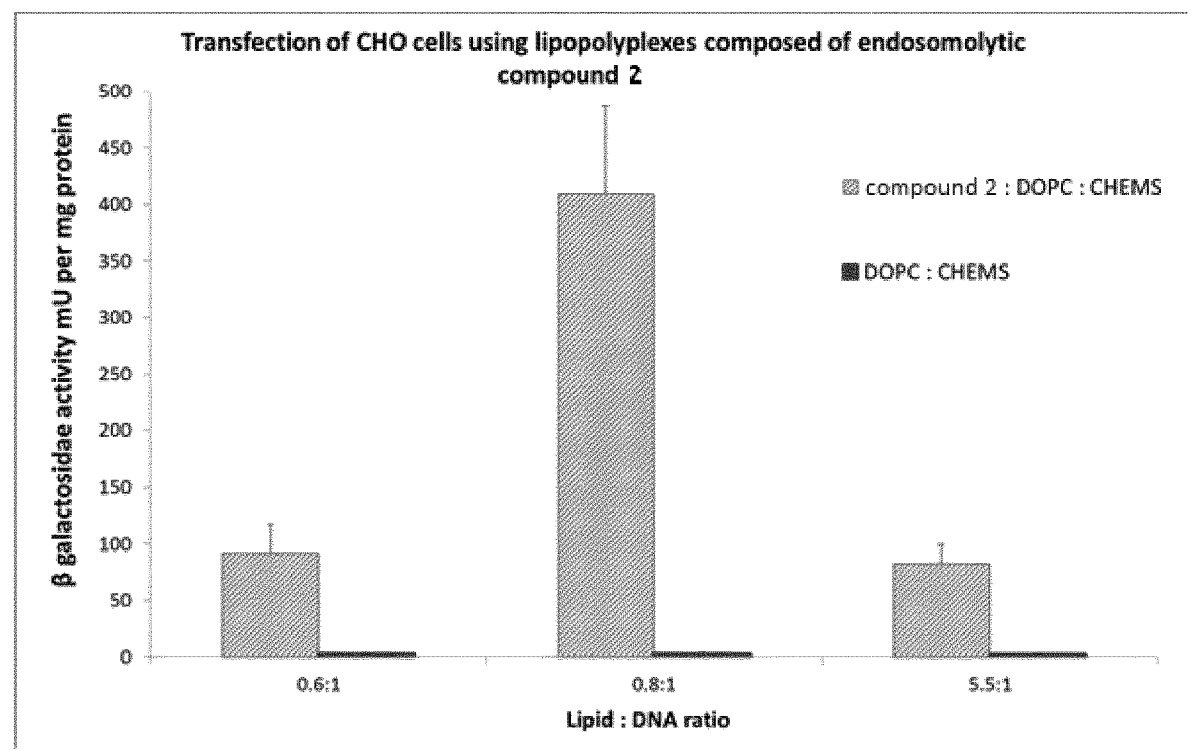
FIG. 2 shows the effect on reporter gene expression of adding an endosomolytic compound to a lipopolyplex, at different lipid:DNA ratios.

Results are show in FIG. 2. Substituting the cholesterol/oleic acid pair with a single moiety containing both a cholesteryl functional group and an anionic carboxylate provided a simpler system for investigating the endosomolytic properties of Compound 2. Thus lipopolyplexes comprising either no Compound 2 or 20 mol % Compound 2 were directly compared with the latter resulting in high, significant levels of β-galactosidase expression over lipid to DNA ratios of 0.6:1 to 5.5:1, with the maximum level observed at 0.8:1 lipid to DNA. This was in contrast to lipopolyplexes prepared in the absence of Compound 2 over the equivalent range of lipid to DNA where expression levels were undetectable, thus confirming the effectiveness of Compound 2 as a transfection enhancing agent.

The data presented herein confirms that compounds of the invention are effective transfection enhancing agent via their endosomolytic properties.

The invention claimed is:

1. A compound of formula (1),

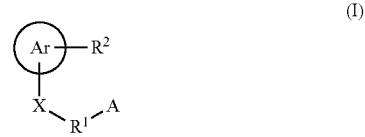

wherein
Ar is an aryl group optionally further substituted with one or more groups $R^3$;
A is a lipophilic, and hydrophobic moiety;
$R^1$ is a phosphodiester, phosphotriester, thioether or amide group;
X is an unsubstituted or substituted $C_6$ to $C_{24}$ alkylene or alkenylene group,
which is optionally interrupted by one or more —$NR^9$—, —O— or —S— linkages,
wherein $R^9$ is a $C_1$ to $C_6$ alkyl group;
$R^2$ is —$YC(R^4)(R^5)CO_2R^6$;
Y is a covalent bond or —$(CH_2)_m$—, wherein m is 1, 2 or 3;
$R^4$ and $R^5$ are the same or different and each is a substituted or unsubstituted $C_1$ to $C_6$ alkyl, $C_2$ to $C_6$ alkenyl or $C_2$ to $C_6$ alkenyl group;
$R^6$ is a hydrogen atom or an unsubstituted or substituted $C_1$ to $C_6$ alkyl group;
each $R^3$ moiety is the same or different and each is selected from a halogen atom, a $C_1$ to $C_6$ alkyl group, a $C_1$ to $C_6$ alkenyl group, a $C_1$ to $C_6$ alkynyl group, a $C_1$ to $C_6$ alkoxy group, and —$YC(R^4)(R^5)CO_2R^6$, and wherein when an $R^3$ moiety is —$YC(R^4)(R^5)CO_2R^6$ it may be the same or different to $R^2$;
wherein $R^4$, $R^5$ and $R^6$ are unsubstituted or substituted with 1, 2 or 3 substituents selected from a halogen atom, a hydroxyl group, $C_1$ to $C_6$ alkoxy and $NR^7R^8$, wherein $R^7$ and $R^8$ are the same or different and each is a $C_1$ to $C^6$ alkyl group;
or a pharmaceutically acceptable salt or solvate thereof.

2. A compound of formula (I) as depicted in claim 1, or a pharmaceutically acceptable salt or solvate thereof, wherein either A is —$R^{10}CH(OR^{12})R^{11}CH(OR^{13})Z$, wherein $R^{12}$ and $R^{13}$ are the same or different and each is a $C_{10}$ to $C_{24}$ alkyl or alkenyl group, $R^{10}$ and $R^{11}$ are the same or different and each is a covalent bond or a —$(CH_2)_s$— group wherein s is 1, 2 or 3, Z is a hydrogen atom or a $C_1$ to $C_3$ alkyl group: or A is an unsubstituted or substituted $C_{17}$ to $C_{35}$ group comprising the fused ring system of a steroid.

3. A compound of formula (I) as depicted in claim 1, or a pharmaceutically acceptable salt or solvate thereof, wherein A is (R)-2,3-di(octadecyloxy)propyl or cholesteryl.

4. A compound of formula (I) as depicted in claim 1, or a pharmaceutically acceptable salt or solvate thereof, wherein the aryl group Ar is a phenyl group.

5. A compound of formula (I) as depicted in claim 1, or a pharmaceutically acceptable salt or solvate thereof, which comprises at least one $R^3$ group which is of the formula —$YC(R^4)(R^5)CO_2R^6$ and is the same or different to the group $R^2$.

6. A compound of formula (I) as depicted in claim 1, or a pharmaceutically acceptable salt or solvate thereof, wherein the compound has the structure

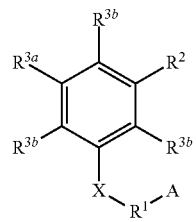

wherein
A is a lipophilic, and hydrophobic moiety;
$R^1$ is a phosphodiester, phosphodiester, thioether or amide group;
X is an unsubstituted or substituted $C_6$ to $C_{24}$ alkylene or alkenylene group,
which is optionally interrupted by one or more —$NR^9$—, —O— or —S— linkages,
wherein $R^9$ is a $C_1$ to $C_6$ alkyl group;
$R^2$ is —$YC(R^4)(R^5)CO_2R^6$;
$R^{3a}$ is of the formula —$YC(R^4)(R^5)CO_2R^6$ and is the same or different to the group $R^2$, and each $R^{3b}$ is the same or different and each is selected from a hydrogen atom, a halogen atom, a $C_1$ to $C_6$ alkyl group, a $C_1$ to $C_6$, alkenyl group, a $C_1$ to $C_6$ alkynl group or a $C_1$ to $C_6$ alkoxy group;
Y is a covalent bond or —$(CH_2)_m$—, wherein m is 1, 2 or 3;
$R^4$ and $R^5$ are the same or different and each is a substituted or unsubstituted $C_1$ to $C_6$ alkyl, $C_2$ to $C_6$ alkenyl or $C_2$ to $C_6$ alkynyl group;
$R^6$ is a hydrogen atom or an unsubstituted or substituted $C_1$ to $C_6$ alkyl group;
each $R^3$ moiety is the same or different and each is selected from a halogen atom, a $C_1$ to $C_6$ alkyl group, a $C_1$ to $C_6$ alkenyl group, a $C_1$ to $C_6$ alkynl group, a $C_1$ to $C_6$ alkoxy group and —$YC(R^4)(R^5)CO_2R^6$, and wherein when an $R^3$ moiety is —$YC(R^4)(R^5)CO_2R^6$ it may be the same or different to $R^2$; and
wherein $R^4$, $R^5$ and $R^6$ are unsubstituted or substituted with 1, 2 or 3 substituents selected from a halogen atom, a hydroxyl group, $C_1$ to $C_6$ alkoxy and $NR^7R^8$, wherein $R^7$ and $R^8$ are the same or different and each is a $C_1$ to $C_6$ alkyl group.

7. A compound of formula (I) as depicted in claim 1, or a pharmaceutically acceptable salt or solvate thereof, wherein $R^1$ is a phosphodiester or phosphotriester group.

8. A compound of formula (I) as depicted in claim 1, or a pharmaceutically acceptable salt or solvate thereof, wherein Y is —$CH_2$—.

9. A compound of formula (I) as depicted in claim 1, or a pharmaceutically acceptable salt or solvate thereof, wherein $R^4$ and $R^5$ are an unsubstituted $C_1$ to $C_6$ alkyl group.

10. A compound of formula (I) as depicted in claim 1, or a pharmaceutically acceptable salt or solvate thereof, wherein $R^6$ is a hydrogen atom or an unsubstituted $C_1$ to $C_3$ alkyl group.

11. A compound of formula (I) as depicted in claim 1, or a pharmaceutically acceptable salt or solvate thereof, wherein X is —$(CH_2)_n$— wherein n is 10 to 20.

12. A compound of formula (I) as depicted in claim 1, or a pharmaceutically acceptable salt or solvate thereof, wherein the compound is one of the following:
dimethyl 3,3'-(5-(11-(((2-chlorophenoxy)(((3R,10R,13R)-10,13-dimenthyl-17-(6-methylheptan-2-yl)-2,3,4,7,8,9,10,11,12,13,14,15,16,17-tetradecahydro-1H-cyclopenta[a]phenanthren-3-yl)oxy)phosphoryl)oxy)undecyl)-1,3-phenylene)bis(2,2-dimethylpropanoate);
3,3'-(5-(11-(((((3R,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)(hydroxy)phosphoryl)oxy)undecyl)-1,3-phenylene)bis(2,2-dimethylpropanoic acid), ammonium salt;
dimethyl 3,3'-(5-(11-((((S)-2,3-bis(octadecyloxy)propoxy)(2-chlorophenoxy)phosphoryl)oxy)undecyl)-1,3-phenylene)bis(2,2-dimethylpropanoate);
3,3'-(5-(11-((((S)-2,3-bis(octadecyloxy)propoxy)(hydroxy)phosphoryloxy)undecyl)-1,3-phenylene)bis(2,2-dimethylpropanoic acid), ammonium salt;

dimethyl 3,3'-(5-(17-(((2-chlorophenoxy)(((3R,10R, 13R)-10,13-dimethyl-17-(6-methylheptan-2-yl)-2,3,4, 7,8,9,10,11,12,13,14,15,16,17-tetradecahydro-1H-cyclopenta[a]phenanthren-3-yl)oxy)phosphoryl)oxy) heptadecyl)-1,3-phenylene)bis(2,2-dimethylpropanoate); or 3,3'-(5-(17-(((((3R,10R,13R)-10,13-dimethyl-17-(6-methylheptan-2-yl)-2,3,4,7,8,9,10,11,12,13,14,15,16, 17-tetradecahydro-1H-cyclopenta[a]phenanthren-3-yl) oxy)(hydroxy)phosphoryl)oxy)heptadecyl)-1,3-phenylene)bis(2,2-dimethylpropanoic acid), ammonium salt.

13. A gene therapy vector comprising the compound as defined in claim 1.

14. A gene therapy vector according to claim 13, which is a polyplex, lipoplex or lipopolyplex.

15. A gene therapy vector according to claim 14, wherein the lipoplex or lipopolyplex comprises liposomes.

16. A pharmaceutical composition comprising a compound according to claim 1 and a pharmaceutically acceptable carrier or diluent.

17. A method for the treatment of a disorder for which the administration of a gene therapy vector is indicated, which comprises administering to a patient in need of such treatment an effective amount of a compound according to claim 1 in conjunction with a gene therapy vector.

18. A method according to claim 1, wherein the compound according to claim 1 is administered simultaneously, sequentially or separately from the gene therapy vector.

19. A method according to claim 17, wherein the gene therapy vector is polyplex, lipoplex or lipopolyplex.

20. A method according to claim 19, wherein the lipoplex or lipopolyplex comprises liposomes.

21. A pharmaceutical composition comprising a gene therapy vector according to claim 13 and a pharmaceutically acceptable carrier or diluent.

* * * * *